US010569100B2

(12) United States Patent
Sepahvandi

(10) Patent No.: US 10,569,100 B2
(45) Date of Patent: Feb. 25, 2020

(54) RETINAL TISSUE REGENERATION

(71) Applicant: Azadeh Sepahvandi, Tehran (IR)

(72) Inventor: Azadeh Sepahvandi, Tehran (IR)

( * ) Notice: Subject to any disclaimer, the term of this patent is extended or adjusted under 35 U.S.C. 154(b) by 151 days.

(21) Appl. No.: 15/706,722

(22) Filed: Sep. 17, 2017

(65) Prior Publication Data
US 2018/0050220 A1    Feb. 22, 2018

Related U.S. Application Data

(60) Provisional application No. 62/405,923, filed on Oct. 9, 2016.

(51) Int. Cl.
| | |
|---|---|
| *A61N 5/06* | (2006.01) |
| *A61L 27/26* | (2006.01) |
| *A61L 27/10* | (2006.01) |
| *B05D 1/00* | (2006.01) |
| *A61K 41/00* | (2020.01) |
| *A61F 9/008* | (2006.01) |
| *A61F 9/007* | (2006.01) |

(52) U.S. Cl.
CPC .......... *A61N 5/062* (2013.01); *A61K 41/0023* (2013.01); *A61L 27/10* (2013.01); *A61L 27/26* (2013.01); *B05D 1/007* (2013.01); *A61F 9/00727* (2013.01); *A61F 2009/00863* (2013.01); *A61L 2430/16* (2013.01); *A61N 2005/0663* (2013.01); *C12N 2533/40* (2013.01)

(58) Field of Classification Search
CPC ................ A61N 5/062; A61K 41/0019; A61K 41/0023; A61K 41/0038; A61L 27/10; A61L 27/26; A61L 27/446; B05D 1/007; C09K 11/02; C09K 11/7773; C09K 11/7792; A61F 9/00727; A61F 2009/00863
See application file for complete search history.

(56) References Cited

U.S. PATENT DOCUMENTS

2014/0336514 A1*  11/2014  Peyman ................. A61N 5/062
                                                    600/473

FOREIGN PATENT DOCUMENTS

CN          105126162 A       12/2015

OTHER PUBLICATIONS

Chen, H., et al., Electrospun chitosan-graft-poly (ϵ-caprolactone)/poly (ϵ-caprolactone) nanofibrous scaffolds for retinal tissue engineering. International Journal of Nanomedicine, 2011. 6: p. 453.
(Continued)

*Primary Examiner* — David H Willse
*Assistant Examiner* — Tiffany P Shipmon
(74) *Attorney, Agent, or Firm* — Bajwa IP Law Firm; Haris Zaheer Bajwa

(57) ABSTRACT

Disclosed herein is a method for regenerating retinal tissue which includes preparing a luminescent scaffold, implanting the luminescent scaffold in a portion of retina, for example subretinal area, emitting a green light from the luminescent nanoparticles in a luminescence phenomenon, and absorbing the emitted light by retinal cells for regenerating retinal tissue by stimulating the retinal cells. Moreover, preparing a luminescent scaffold may comprise synthesizing a plurality of luminescent particles, dispersing the luminescent particles in a polymeric matrix to form a luminescent composite, and electrospinning the luminescent composite to form the luminescent scaffold.

19 Claims, 30 Drawing Sheets

(56) References Cited

OTHER PUBLICATIONS

Palanker, D., et al., Design of a high-resolution optoelectronic retinal prosthesis. Journal of Neural Engineering, 2005. 2(1): p. S105.

Chen, F., et al., The photoluminescence, drug delivery and imaging properties of multifunctional Eu 3+/Gd 3+ dual-doped hydroxyapatite nanorods. Biomaterials, 2011. 32(34): p. 9031-9039.

Chen, G., et al.,(α-NaYbF4: Tm3+)/CaF2 core/shell nanoparticles with efficient near-infrared to near-infrared upconversion for high-contrast deep tissue bioimaging. ACS nano, 2012. 6(9): p. 8280-8287.

Zhao, C., et al., Synthesis of Sr 4 Al 14 O 25: Eu 2+, Dy 3+ phosphor nanometer powders by combustion processes and its optical properties. Materials Science and Engineering: B, 2006. 133(1): p. 200-204.

Chen, I.-C. and T.-M. Chen, Sol-gel synthesis and the effect of boron addition on the phosphorescent properties of SrAl2O4: Eu2+, Dy3+ phosphors. Journal of Materials Research, 2001. 16(3): p. 644-651.

* cited by examiner

RETINAL TISSUE REGENERATION

CROSS-REFERENCE TO RELATED APPLICATION

This application claims the benefit of priority from U.S. Provisional Patent Application Ser. No. 62/405,923, filed on Oct. 9, 2016, and entitled "RETINAL TISSUE REGENERATION BY BIOCOMPATIBLE SRAL2O4:EU2+DY3 LUMINESCENCE NANOPARTICLES," which is incorporated herein by reference in its entirety.

TECHNICAL FIELD

The present disclosure generally relates to tissue engineering, particularly to retinal tissue regeneration, and more particularly to retinal tissue regeneration by luminescence particles.

BACKGROUND

Retina is one of the well-developed structures of eyes with several layers of neurons, which are interconnected by synapses. Degenerative retinal diseases such as retinitis pigmentosa and age-related macular affects millions of people, and without any treatment, these diseases lead to an irreversible blindness. In order to treat degenerative retinal diseases, extensive research has been conducted and various treatment approaches have been proposed, such as drug therapy, gene therapy, cell therapy, artificial retinas, and tissue engineering.

In retinal tissue engineering, retinal implant restores useful vision for limited visual abilities by stimulating the surviving retinal nerve cells. It is also advantageous in increasing cell survival and directing stem cells or progenitor cell differentiate toward a photoreceptor state. In retinal tissue engineering, biocompatibility, non-toxicity, ability to excrete proper signals and compatible physical characteristics are essential features of the treatment method.

Recent advances in fabrication of polymers such as polyglycolic acid (PGA), polylactic acid (PLLA), poly-DL-lactic acid (PDLLA), hyaluronic acid (HA), polycaprolactone (PCL), and chitosan (CS) led to development of polymeric scaffolds which are implanted in retina area; however, absence of proper signaling in these polymeric scaffolds wouldn't result in an expected improvement in regeneration of retina.

Different signals like chemical, mechanical and electrical signals can affect cellular behavior in a tissue regeneration process. Electromagnetic waves, for example light, are the most effective signals for retinal cells. Therefore, there is a need in the art to provide tissue engineering scaffolds with better mechanical and optical properties to improve cell growth and cell differentiation, particularly in retina. Also, there is a need for a polymeric scaffold with the ability of producing proper electromagnetic signals for improving retina regeneration.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In exemplary embodiments consistent with the present disclosure, a method for regenerating retinal tissue is disclosed. The method may include preparing a luminescent scaffold, implanting the luminescent scaffold in a portion of retina, emitting a green light from the luminescent nanoparticles in a luminescence phenomenon, and absorbing the emitted light by retinal cells for regenerating retinal tissue by stimulating the retinal cells.

In some exemplary embodiments, preparing the luminescent scaffold may comprise synthesizing a plurality of luminescent particles, dispersing the luminescent particles in a polymeric matrix to form a luminescent composite, and electrospinning the luminescent composite to form the luminescent scaffold. In an exemplary embodiment, the portion of the retina may comprise subretinal area.

In an exemplary embodiment, the luminescent scaffold may include a polymeric matrix in which a plurality of luminescent particles may be dispersed. Moreover, the luminescent scaffold may further include poly ethylene glycol (PEG), which may be present in the scaffold with a concentration between about 5 mg/ml and about 15 mg/ml, for example 10 mg/ml.

In an exemplary embodiment, the luminescent particles may be biocompatible particles, and the biocompatible particles may include poly ethylene glycol (PEG). In an exemplary embodiment, the luminescent particles may be PEGylated by PEG. The luminescent particles may include nanoparticles.

According to some exemplary embodiments, the luminescent particles may include ceramic particles, which may include $SrAl_2O_4:Eu^{2+}Dy3$ particles, or $NaYF_4:Yb^{3+}Er^{3+}$ particles, or combinations thereof. The polymeric matrix of the scaffold may include a copolymer of two or more polymers, for example, a copolymer of polycaprolactone (PCL) and chitosan (CS).

According to an exemplary embodiment, the luminescent particles may be present in the scaffold with a concentration between about 5 mg/ml and about 15 mg/ml. According to an exemplary embodiment, synthesizing the plurality of luminescent particles may comprise synthesizing the plurality of luminescent particles using one of sol gel method, co-precipitation method, and combinations thereof.

According to some exemplary embodiments, dispersing the luminescent particles in the polymeric matrix may comprise dispersing the luminescent particles in the polymeric matrix using a homogenizer, a stirrer, an agitator, a sonicator, an ultrasound device, and combinations thereof.

According to an exemplary embodiment, electrospinning the luminescent composite may comprise feeding the luminescent composite through an electrospinning column with a feeding rate of about 1 mL/hour. Electrospinning the luminescent composite may comprise pumping the luminescent composite into an electrospinning column. The electrospinning column may comprise a needle with a gauge of about 17.

According to an exemplary embodiment, electrospinning the luminescent composite may comprise applying an electric field with a strength of about 15 kV/20 cm between an electrospinning column and a collecting plate.

Other systems, methods, features and advantages of the exemplary embodiments will be, or will become, apparent to one of ordinary skill in the art upon examination of the following figures and the accompanying detailed description. It is intended that all such additional systems, methods, features and advantages be included within this description and this summary, be within the scope of the consistent with exemplary embodiments of the present disclosure, and be protected by the following claims.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Treating retina diseases, such as retinitis pigmentosa and age-related macular degeneration has a great importance. One way to treat these diseases may include tissue regeneration of retina. The present disclosure is directed to a method for retinal tissue engineering, for example, retina regeneration, with an improved biological, mechanical, optical, and degradation properties.

The method of the present disclosure may include preparing a luminescent scaffold, implanting the luminescent scaffold in a portion of retina, emitting a green light from the luminescent nanoparticles in a luminescence phenomenon, and absorbing the emitted light by retinal cells for regenerating retinal tissue by stimulating the retinal cells.

In some exemplary embodiments, preparing the luminescent scaffold may comprise synthesizing a plurality of luminescent particles, dispersing the luminescent particles in a polymeric matrix to form a luminescent composite, and electrospinning the luminescent composite to form the luminescent scaffold. In an exemplary embodiment, the portion of the retina may comprise subretinal area.

As used herein, the term "luminescence" refers to an emission of light by a substance that has not been heated, as in a phosphorescence phenomenon. Moreover, the term "PEGylation" may be understood to refer to a process of both covalent and non-covalent attachment of polyethylene glycol (PEG) polymer chains to molecules and macrostructures, such as a drug, or luminescent particles, which are then described as PEGylated luminescent particles.

Figure 1:
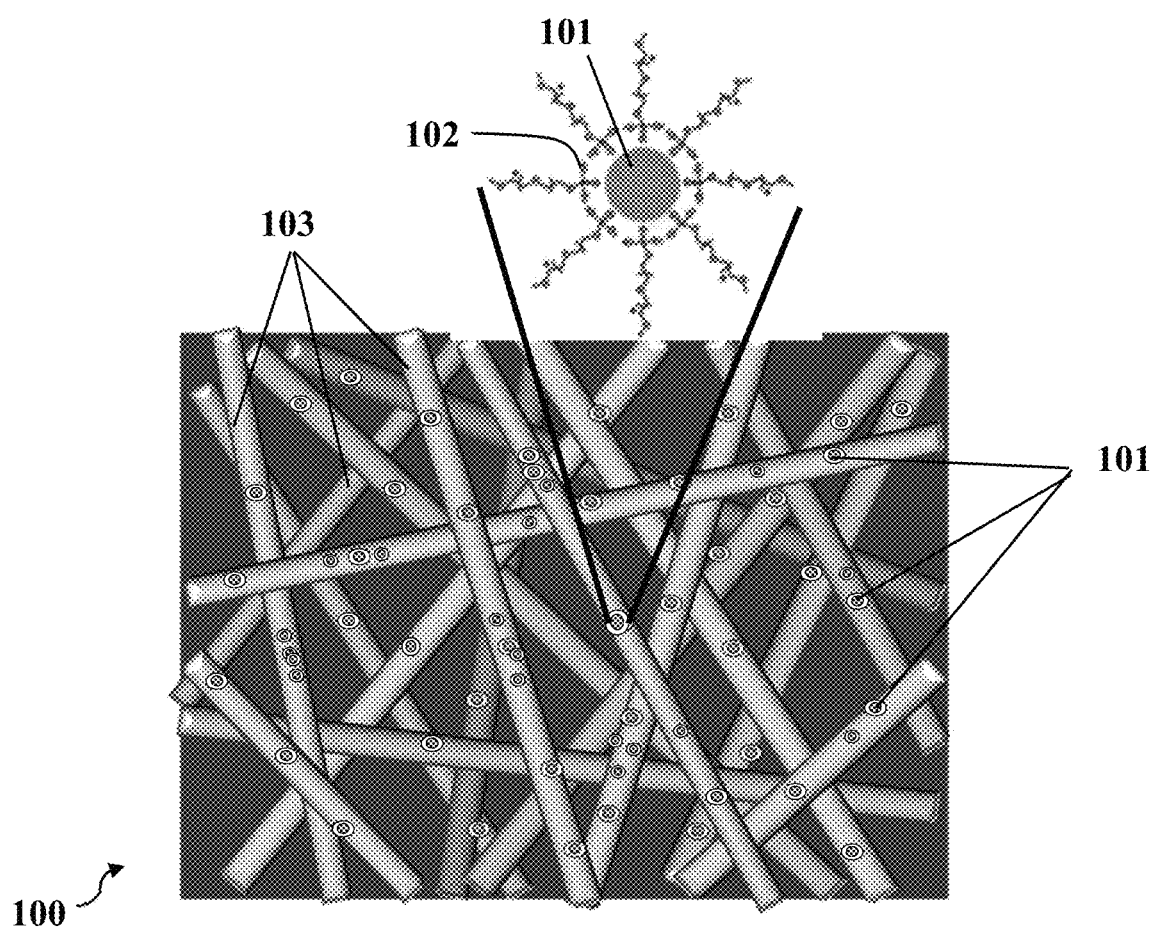
FIG. 1 illustrates a schematic of a luminescent scaffold, consistent with an exemplary embodiment of the present disclosure.

FIG. 1 illustrates a schematic of a luminescent scaffold 100 for regenerating retinal tissue, consistent with an exemplary embodiment of the preset disclosure. The scaffold 100 may include luminescent particles 101 and a polymeric matrix 103. In an exemplary embodiment, the scaffold 100 may further include poly ethylene glycol (PEG) 102, which may be used for PEGylation the luminescent particles 101, so that the luminescent particles 101 may be coated by the PEG 102.

The luminescent particles 101 may include biocompatible particles, which may be PEGylated by PEG 102 to obtain and improve biocompatibility properties. The Luminescent particles 101 may include nanoparticles with an average size of about 100 nm or less. The luminescent particles 101 may include ceramic particles, for example, $SrAl_2O_4:Eu^{2+}Dy^{3+}$ particles, or $NaYF_4:Yb^{3+}Er^{3+}$ particles, or combinations thereof. Moreover, the luminescent particles 101 may be present in the scaffold 100 with a concentration between about 5 mg/ml and about 15 mg/ml. The luminescent particles 101 may be synthesized by a sol-gel method, a co-precipitation method, or combinations thereof.

In an exemplary embodiment, the luminescent scaffold 100 may include poly ethylene glycol (PEG) 102, which may be present in the luminescent scaffold 100 with a concentration of about between 5 mg/ml and about 15 mg/ml, for example about 10 mg/ml. The presence of PEG 102 may be considered for PEGylation of the luminescent particles which may enhance the biocompatibility of the luminescent particles 101 and the prepared luminescent scaffold 100.

It should be noticed that the structure of the eyeball is such that it focuses the light reaching the eye on retina; so, the retinal cells are in direct contact with the visible light. The luminescent scaffold 100 may be placed in a portion of retina, for example in subretinal area, as an implant. After implanting the luminescent scaffold in the portion of retina, the visible light from external sources of patient's environment may enter the eyeball, and the implanted luminescent scaffold may be exposed to the entered visible light.

Exposure to the visible light may lead the luminescent particles in the luminescent scaffold to be excited; so, the luminescent particles may emit green light in a luminescence phenomenon. After that, retinal cells may be stimulated by absorbing the emitted light from the luminescent scaffold. The stimulation of retinal cells may lead to regenerating retinal tissue.

In an exemplary embodiment, stimulation of the retinal cells may significantly boost their proliferation and their differentiation into retinal neural cells and particularly in photoreceptors cells; therefore, the retina tissue may be regenerated and the retina disease may be treated.

Several parameters may affect the emission light of the luminescent scaffold 100, for example, luminescent particles size, surface properties of the luminescent particles, and thickness of PEGylation. In excitation of the luminescent scaffold 100, when the excitation light reaches the PEGylated luminescence particles, a portion of excitation light may be scattered when it is reaching both the surface of the PEG coating 102 and the interface between the PEG coating 102 and the luminescent particles 101.

Therefore, in case of using PEG in structure of the luminescent scaffold, the optimum concentration of PEG should be determined in regards to acquire a highest emission intensity and a sufficient PEG coating for biocompatibility of the scaffold.

In an exemplary embodiment, the polymeric matrix 103 of the luminescent scaffold 100 may include copolymer fibers of one or more polymers, for example, polycaprolactone (PCL), chitosan (CS), or combinations thereof. The copolymer may have a capability of dispersing ceramic luminescent particles 101. Moreover, the nanofibers of the copolymer and the luminescent scaffold 100 may be prepared via an electrospinning process.

Figure 2A:
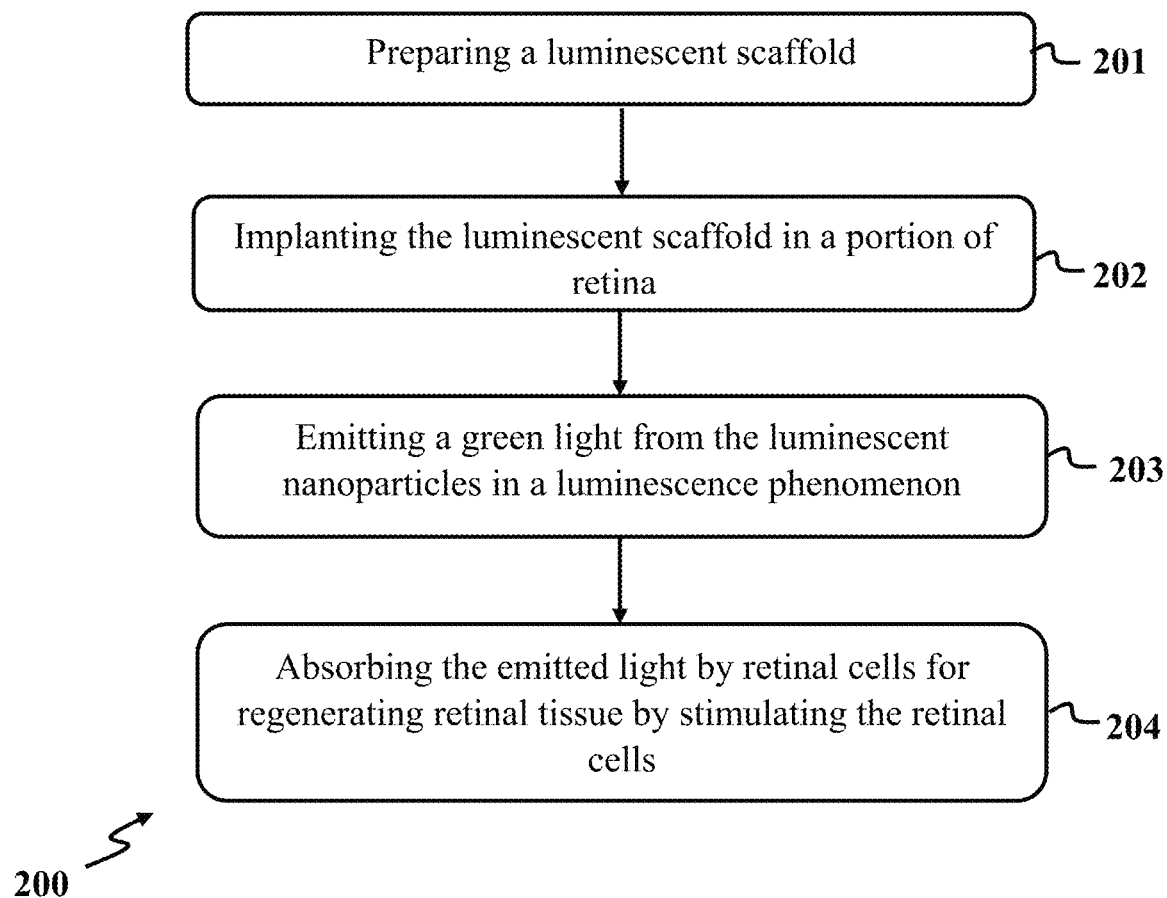
FIG. 2A illustrates a method for forming a luminescent scaffold, consistent with an exemplary embodiment of the present disclosure.

FIG. 2A is a method 200 for regenerating retinal tissue, consistent with an exemplary embodiment of the present disclosure. Method 200 may include preparing a luminescent scaffold (step 201), implanting the luminescent scaffold in a portion of retina (step 202), emitting a green light from the luminescent nanoparticles in a luminescence phenomenon (step 203), and absorbing the emitted light by retinal cells for regenerating retinal tissue by stimulating the retinal cells (step 204).

Step 201 may include preparing the luminescent scaffold. The luminescent scaffold may be prepared utilizing the procedure described in method 210 of FIG. 2B. Preparation of the luminescent scaffold may include synthesizing a plurality of luminescent particles, dispersing the luminescent particles in the polymeric matrix to form a luminescent composite, and electrospinning the luminescent composite to form the luminescent scaffold.

Figure 2B:
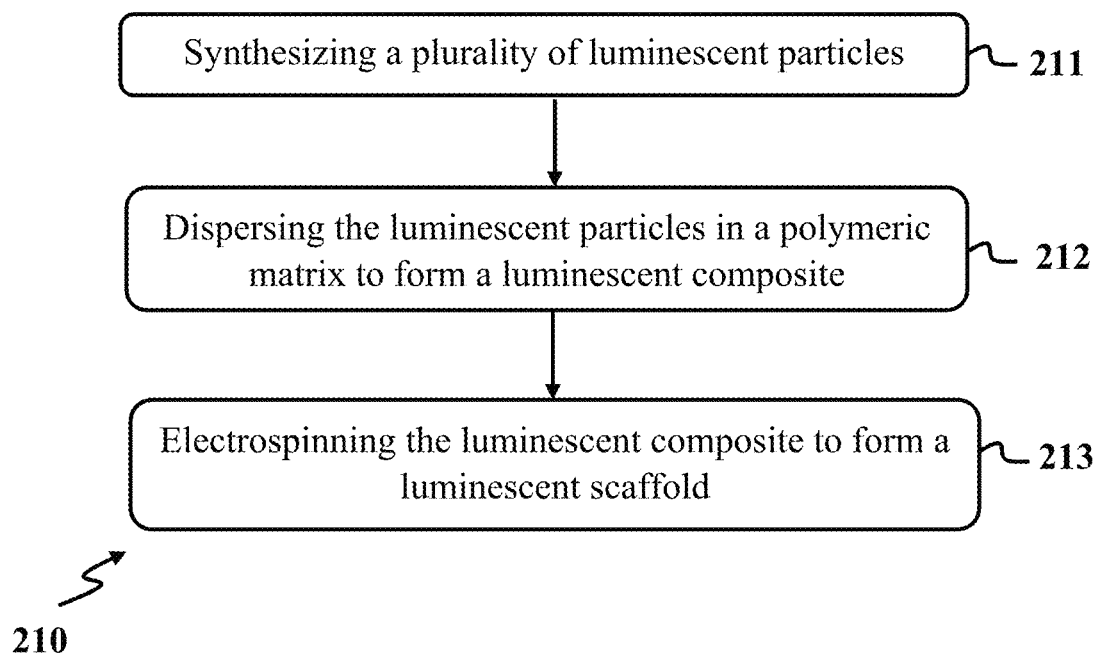
FIG. 2B illustrates a method for regenerating retinal tissue, consistent with an exemplary embodiment of the present disclosure.

FIG. 2B is a method 210 for forming a luminescent scaffold similar to step 201, consistent with an exemplary embodiment of the present disclosure. The method 210 may include synthesizing a plurality of luminescent particles (step 211), dispersing the luminescent particles in the polymeric matrix to form a luminescent composite (step 212), and electrospinning the luminescent composite to form the luminescent scaffold (step 213).

Step 211 may include synthesizing a plurality of luminescent particles. The luminescent particles may be synthesized by a sol-gel method, a co-precipitation method, or combinations thereof. The luminescent particles may include nanoparticles with an average size of about 100 nm or less. The luminescent particles may include ceramic particles, for example, $SrAl_2O_4$: $Eu^{2+}Dy^{3+}$ particles, or $NaYF_4$:$Yb^{3+}Er^{3+}$ particles, or combinations thereof.

In an exemplary embodiment, the luminescent particles may be PEGylated by using poly ethylene glycol (PEG), which may enhance the biocompatibility of the luminescent particles and the prepared luminescent scaffold.

Step 212 may include dispersing the luminescent particles in a polymeric matrix to form a luminescent composite. The luminescent particles may be dispersed in the polymeric matrix to form a luminescent composite. The luminescent particles may be dispersed in the polymeric matrix utilizing a homogenizer, a stirrer, an agitator, a sonicator, an ultrasound device, or combinations thereof.

The polymeric matrix may include copolymer fibers of one or more polymers, for example, polycaprolactone (PCL), chitosan (CS), or combinations thereof. The copolymer may have a capability of dispersing ceramic luminescent particles.

Step 213 may include electrospinning the luminescent composite to form a luminescent scaffold. The luminescent scaffold may be prepared from the luminescent composite in an electrospinning process. Electrospinning is a spinning technique using electrostatic forces to produce fine fibers from polymer solutions or melts; therefore, a fibrous luminescent scaffold may be prepared during the electrospinning process.

The electrospinning process of the luminescent composite may be conducted in following manner. The luminescent composite may be pumped into an electrospinning column that has a needle as a nozzle with a gauge of about 17. The luminescent composite may be fed through the electrospinning column at a feeding rate of about 1 mL/hour.

After that, the power supply may be turned on by applying an electric field with a strength of about 15 kV/20 cm between the electrospinning column as the positive electrode and a collecting plate as the negative electrode. Then the luminescent scaffold may be prepared on the collecting plate during the electrospinning process.

After completing the electrospinning process, the electrospun luminescent scaffold may be placed in a vacuum oven to remove any residual organic solvent from the nonwoven membranes of the scaffold's fibers.

Then getting back to method 200, step 202 may include implanting the luminescent scaffold in a portion of retina. The luminescent scaffold may be placed in a portion of retina as an implant. In an exemplary embodiment, the portion of retina may be subretinal area. Moreover, implanting the luminescent scaffold in the portion of retina may be done through a surgical process. The thickness of the luminescent scaffold may be between about 5 μm and about 250 μm considering the amount of retinal damage.

Step 203 may include emitting a green light from the luminescent nanoparticles in a luminescence phenomenon.

After implanting the luminescent scaffold in the portion of retina, the visible light from external sources of patient's environment may enter the eyeball, and the implanted luminescent scaffold may be exposed to the entered visible light. As a result of exposure to the visible light, the luminescent particles in the luminescent scaffold may be excited, and the luminescent particles may emit green light in a luminescence phenomenon.

Step 204 may include absorbing the emitted light by retinal cells for regenerating retinal tissue by stimulating the retinal cells. The retinal cells may be stimulated by absorbing the emitted light from the luminescent scaffold. The stimulation of retinal cells may lead to regeneration of retinal tissue.

In an exemplary embodiment, stimulation of the retinal cells may significantly boost their proliferation and their differentiation into retinal neural cells and particularly in photoreceptors cells; therefore, the retina tissue may be regenerated and the retina disease may be treated.

EXAMPLES

The following examples describe exemplary embodiments of the preparation method of luminescent particles and the luminescent scaffold of the present disclosure. Furthermore, optical, mechanical, and biological characteristics of different luminescent scaffolds are examined.

Example 1: Synthesis of Luminescent Nanoparticles

The luminescent particles may be applied for retinal tissue engineering, for example, retina regeneration; therefore, luminescent particles may be exposed to different cells in retina, and size of the luminescent particles should be same as the cellular size in nanometer scale. Therefore, the sol-gel method was used in this example to synthesize $SrAl_2O_4$: $Eu^{2+}Dy^{3+}$ particles to obtain the particles with a desired size. In this example, $SrAl_2O_4$:$Eu^{2+}Dy^{3+}$ luminescent nanoparticles were synthesized.

In order to prepare $SrAl_2O_4$:$Eu^{2+}Dy^{3+}$ luminescent nanoparticles with high bright emission and long afterglow, $Eu^{2+}Dy^{3+}$ co-doped strontium aluminate ($SrAl_2O_4$) luminescent nanoparticles were prepared as follows. At first, analytical graded reagents such as aluminum nitrate (Al$(NO_3)_3$), strontium nitrate ($Sr(NO_3)_2$), dysprosium nitrate ($Dy(NO_3)_3$) and europium nitrate ($Eu(NO_3)_3$) were dissolved in distilled water with the following molar ratios: ($Sr(NO_3)_2$ 0.97, $Eu(NO_3)_3$ 0.01, $Dy(NO_3)_3$ 0.02); then, an $AL_2O_4$ solution as a reducing agent with a concentration of about 1 molar was added to the solution of the analytical graded reagents in distilled water to form a first solution. Doping rates of $Eu^{2+}$ and the $Dy^{3+}$ co-dopants were established in a way that result the longest and the most intense afterglow.

After that, in order to form a gel that includes $SrAl_2O_4$: $Eu^{2+}Dy^{3+}$ luminescent nanoparticles, polyethylene glycol (PEG) with a molecular weight of 2000 as a disperser and an ammonium bicarbonate ($NH_4HCO_3$) solution were added dropwise to the first solution under stirring condition until a second solution with pH of about 5 was formed. The $NH_4HCO_3$ solution had a concentration of about 0.1 molar solution, and it included about 1% (weight/weight) PEG 600. Stirring the second solution was continued for about 2 hours at a temperature of about 80° C. to form a gel. Thereafter, citric acid was added to the gel with a molar ratio of about 1:1.

After that, in order to remove water content of the resulting gel, the gel was dried and fired in an electrical furnace with a firing rate of about 10° C./minute and at a temperature of about 1200° C. Then, in order to stabilize the gel, the gel was placed in an active carbon atmosphere at a temperature of about 1200° C. for 16 about hours.

In the next step, in order to increase the biocompatibility of the synthesized luminescent nanoparticles, they were PEGylated. Different concentrations of poly ethylene glycol 4000 (PEG) were dissolved in deionized water, for example in order to form a transparent solution, about 10 grams of PEG 4000 was added to about 10 milliliter of deionized water, and then the synthesized $SrAl_2O_4:Eu^{2+}Dy^{3+}$ luminescent nanoparticles were added to the resultant solutions to form mixtures.

After keeping the mixtures in a stationary mode for about 10 hours, they were placed in an ultrasonic bath for about 45 minutes. After that, PEGylated $SrAl_2O_4:Eu^{2+}Dy^{3+}$ luminescent nanoparticles were washed with distilled water and were centrifuged. Finally, the obtained luminescent nanoparticles were dried by exposing to air for about 24 hours.

Transmission electron microscopy (TEM) at an accelerating voltage of 80 kV was used to characterize the morphology of the $SrAl_2O_4:Eu^{2+}Dy^{3+}$ luminescent nanoparticles before and after PEGylation.

Figure 3A:
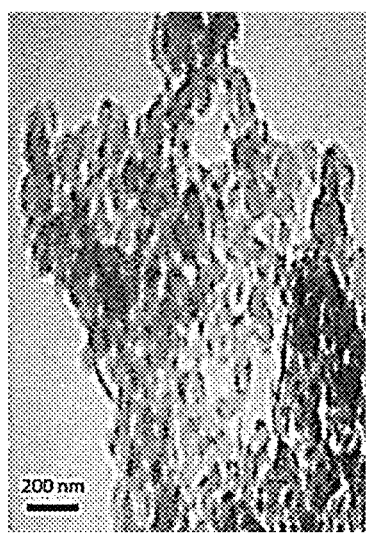
FIG. 3A illustrates a transmission electron microscopy (TEM) image of the aggregated $SrAl_2O_4:Eu^{2+}Dy^{3+}$ luminescent nanoparticles, consistent with an exemplary embodiment of the present disclosure.

FIG. 3A illustrates a transmission electron microscopy (TEM) image of the aggregated $SrAl_2O_4:Eu^{2+}Dy^{3+}$ luminescent nanoparticles without PEGylation. Referring to FIG. 3A, the $SrAl_2O_4:Eu^{2+}Dy^{3+}$ luminescent nanoparticles are not dispersible in water, and they have a higher surface energy than bigger particles; therefore, they have a tendency for agglomeration.

Figure 3B:
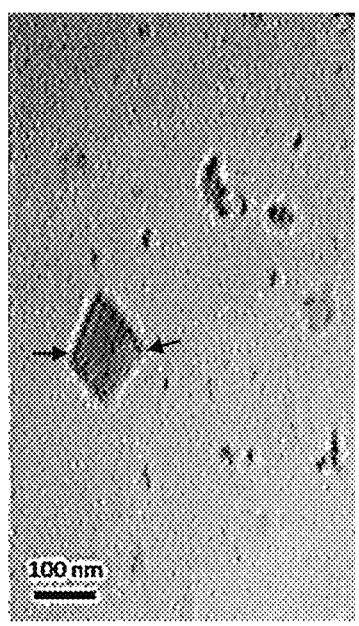
FIG. 3B illustrates a transmission electron microscopy (TEM) image of the magnified $SrAl_2O_4:Eu^{2+}Dy^{3+}$ luminescent nanoparticles, consistent with an exemplary embodiment of the present disclosure.

FIG. 3B illustrates a transmission electron microscopy (TEM) image of the magnified $SrAl_2O_4:Eu^{2+}Dy^{3+}$ luminescent nanoparticles, consistent with an exemplary embodiment of the present disclosure. The average particle size of $SrAl_2O_4:Eu^{2+}Dy^{3+}$ luminescent nanoparticles are approximately 50 nm.

Figure 3C:
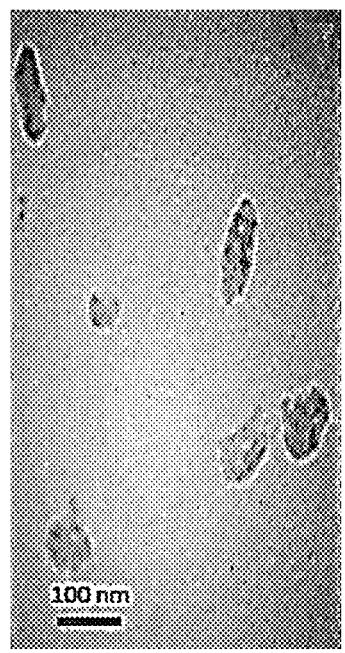
FIG. 3C illustrates a transmission electron microscopy (TEM) image of PEGylated $SrAl_2O_4:Eu^{2+}Dy^{3+}$ luminescent nanoparticles, consistent with an exemplary embodiment of the present disclosure.

FIG. 3C illustrates a transmission electron microscopy (TEM) image of PEGylated $SrAl_2O_4:Eu^{2+}Dy^{3+}$ luminescent nanoparticles, consistent with an exemplary embodiment of the present disclosure. It is hard to recognize PEG layers in this TEM image, because the PEG molecules have a poor contrast due to their low electron density, and the PEG coating may be damaged during the preparation technique.

Referring to FIGS. 3B, and 3C, it is apparent that $SrAl_2O_4:Eu^{2+}Dy^{3+}$ nanoparticles have a sharp edged form, but after PEGylation the corners were rounded by coating particles. The luminescent particles with rounded corners have a uniform surface charge, and as a result, these particles increase convergence among nanofibers in agglomeration; therefore, this deformation improves mechanical characteristics of a scaffold which is prepared by using the luminescent particles.

Example 2: Preparation of the Luminescent Scaffold

In this example, a scaffold with $SrAl_2O_4:Eu^{2+}Dy^{3+}$ luminescent nanoparticles was prepared utilizing the following steps. At first, a copolymer of chitosan and polycaprolactone (CS-PCL) was prepared by grafting ε-caprolactone oligomers (PCL) onto hydroxyl groups of chitosan (CS). Therefore, about 2.0 grams of CS, which has about 12 mmol of glucosamine units, and about 20 mL of $MeSO_3H$ was inserted to a flame-dried 50 mL flask to form a solution. In order to dissolve chitosan (CS) completely, the solution was stirred for approximately 30 minutes at 45° C.

After that, about 16.58 grams of ε-caprolactone monomer was injected to the solution to form a copolymer mixture. The copolymer mixture was stirred for about 5 hours under nitrogen atmosphere at a temperature of about 45° C.; then the copolymer mixture was filtered to collect the resulting CS-PCL copolymer. After that, in order to adjust the filtrate pH, the filtrate was added into a solution containing about 250 mL of about 0.2 molar $KH_2PO_4$, about 40 mL of about 10 molar NaOH, and 100 grams of crushed ice. The final product of CS-PCL copolymer was washed with distilled water several times and freeze-dried under vacuum at about −56° C. for about 3 days.

In order to examine the graft copolymerization of PCL onto CS by the free amino groups of CS, the copolymer mixture of CS-PCL was studied by FT-IR spectroscopy.

Figure 4:
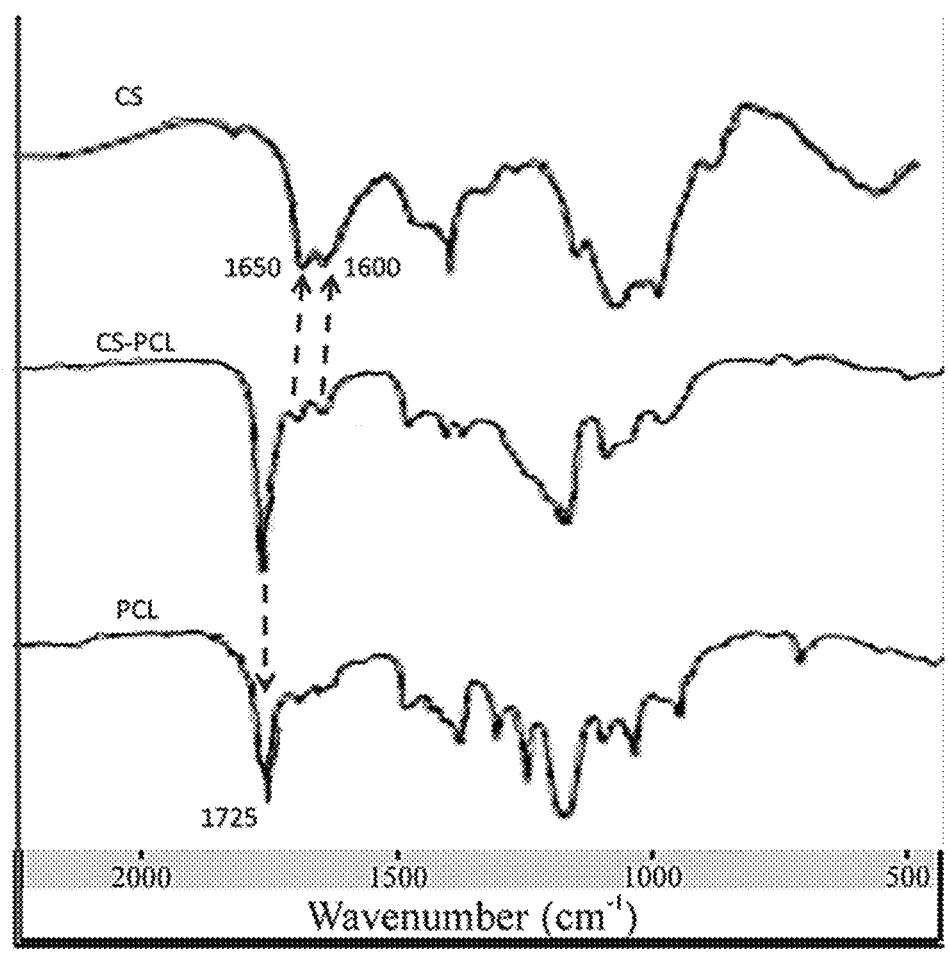
FIG. 4 illustrates the Fourier-transform infrared spectra of CS-PCL copolymer in comparison with chitosan (CS) and polycaprolactone (PCL), consistent with an exemplary embodiment of the present disclosure.

FIG. 4 illustrates Fourier-transform infrared spectra of CS-PCL copolymer in comparison with chitosan (CS) and polycaprolactone (PCL), consistent with an exemplary embodiment of the present disclosure. Referring to FIG. 4, the FTIR spectra of CS-PCL has three absorbance bands at wavelengths of about 1725 $cm^{-1}$, 1650 $cm^{-1}$, and 1600 $cm^{-1}$, which were allocated to the peculiar bands of ester in PCL, amide I band, and amino groups in CS, respectively. These peaks confirm the proper graft copolymerization of PCL onto CS.

In the next step, in order to obtain a solution for producing electrospun nanofiber, the produced CS-PCL copolymer was dissolved in a solution containing dimethyl formamide/chloroform with a concentration ratio of about 1:4 (volume/volume). Then, the resultant mixtures were stirred for about 24 hours to obtain a homogenous copolymer solution.

After that, the $SrAl_2O_4:Eu^{2+}Dy^{3+}$ luminescent nanoparticles, which were synthesized according to EXAMPLE 1, were modified by phosphoric acid and then they were coated with PEG with a concentration of about 10 mg/ml. Afterward, PEGylated luminescent particles with concentrations of about 10%, about 30%, and about 50% of weight of the copolymer solution were dispersed into the three homogenous copolymer solutions to form luminescent composites. Then, the luminescent composites were magnetically stirred for about 12 hours until uniform luminescent composites were obtained.

A lot of measurements were employed in order to prevent agglomeration and bead formations, since it is assumed that they affect the luminescence characteristics of the luminescent particles. At first, $SrAl_2O_4:Eu^{2+}Dy^{3+}$ luminescent nanoparticles dispersion was promoted by adding water content to the solution. However, as the concentration of the particles in electrospun solution increases, the bead formation is delayed.

The dispersion status of the luminescent composites was controlled by sonication with a power between about 3 W and about 9 W to obtain agglomerated samples (by sonication at 3 W) and dispersed samples (by sonication at 9 W). The sonication time was kept constant at 10 minutes.

Moreover, several parameters such as the viscosity of the dilution, feeding rate, electric field strength, and relative humidity were closely monitored during the preparation and electrospinning process. Furthermore, the compatibility of luminescent particle size to scaffold fibers diameter, which was a critical parameter in smoothness and uniformity of the resultant scaffolds, were measured.

After that, an electrospinning system was used to prepare luminescent scaffolds from produced luminescent composites. At first, a syringe was filled with about 5 ml of the prepared luminescent composite. Then, the luminescent composite was pumped at a feeding rate of about 1 ml/h. Also, the metal needle with about 17 gauge of the syringe was connected to a high voltage power supply; and for starting the electrospinning, the electric field strength was kept at about 15 kV/20 cm.

After completing the electrospinning process, the electrospun luminescent scaffold was placed in a vacuum oven at 60° C. for about 12 hours to remove any residual organic solvent from the nonwoven membranes of the scaffold's fibers. The electrospinning process was repeated for three prepared luminescent composites to form different luminescent scaffolds.

Figure 5A:
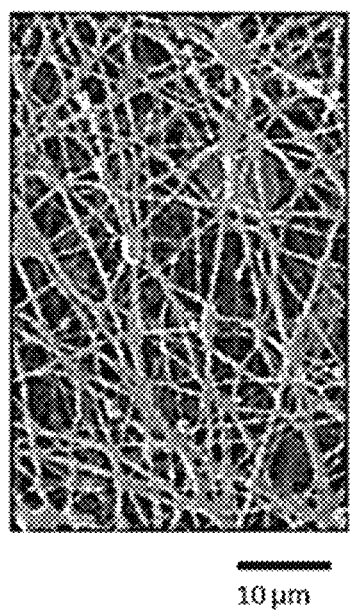
FIG. 5A illustrates a scanning electron microscopy (SEM) image of a CS-PCL scaffold as a control group, consistent with an exemplary embodiment of the present disclosure.
Figure 5B:
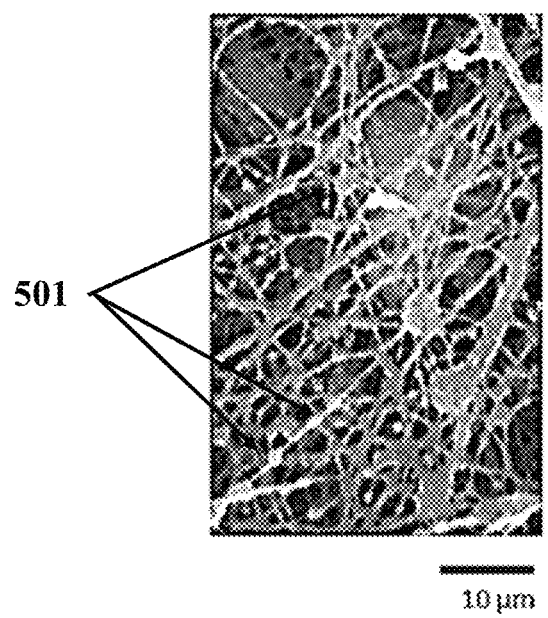
FIG. 5B illustrates a scanning electron microscopy (SEM) image of $SrAl_2O_4: Eu^{2+}Dy^{3+}$/CS-PCL luminescent scaffold with 10% luminescent nanoparticles, consistent with an exemplary embodiment of the present disclosure.

Moreover, morphology of luminescent scaffolds was studied before and after dispersion of $SrAl_2O_4:Eu^{2+}Dy^{3+}$ luminescent nanoparticles into the CS-PCL copolymer. FIG. 5A illustrates a scanning electron microscopy (SEM) image of CS-PCL scaffold as a control group. FIG. 5B illustrates a scanning electron microscopy (SEM) image of $SrAl_2O_4$: $Eu^{2+}Dy^{3+}$/CS-PCL luminescent scaffold with 10% luminescent particles. Some agglomerations 501 are observed in the scaffolds due to the aggregation of the luminescent particles.

Figure 5C:
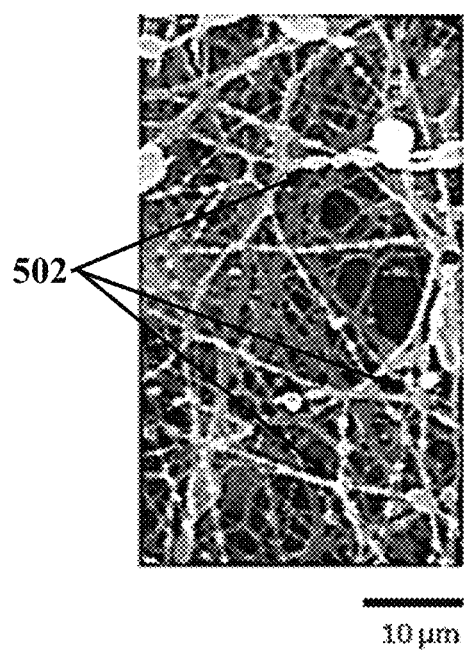
FIG. 5C illustrates a scanning electron microscopy (SEM) image of $SrAl_2O_4: Eu^{2+}Dy^{3+}$/CS-PCL luminescent scaffold with 30% luminescent nanoparticles, consistent with an exemplary embodiment of the present disclosure.

FIG. 5C illustrates a scanning electron microscopy (SEM) image of $SrAl_2O_4$: $Eu^{2+}Dy^{3+}$/CS-PCL luminescent scaffold with 30% luminescent nanoparticles. More agglomerations 502 are formed in the scaffolds duo to the aggregation of the luminescent particles in comparison with the scaffold with 10% luminescent nanoparticles.

Figure 5D:
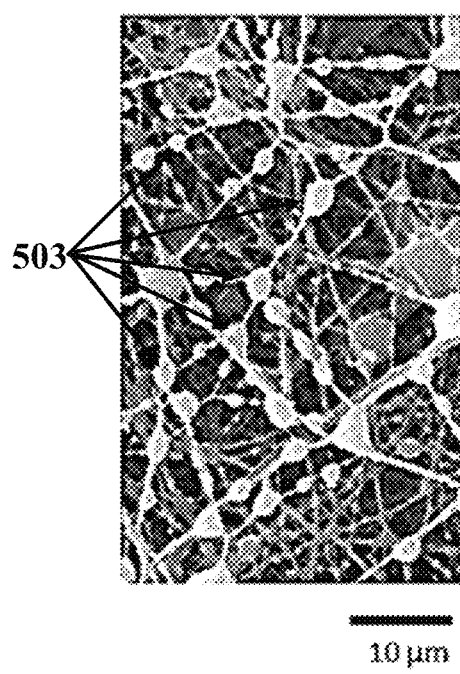
FIG. 5D illustrates a scanning electron microscopy (SEM) image of $SrAl_2O_4: Eu^{2+}Dy^{3+}$/CS-PCL luminescent scaffold with 50% luminescent nanoparticles, consistent with an exemplary embodiment of the present disclosure.

FIG. 5D illustrates a scanning electron microscopy (SEM) image of $SrAl_2O_4$: $Eu^{2+}Dy^{3+}$/CS-PCL luminescent scaffold with 50% luminescent nanoparticles. More agglomerations 503 are formed in the scaffolds duo to the aggregation of the luminescent particles in comparison with other luminescent scaffolds.

Referring to FIGS. 4A-4D, by increasing the percentage of luminescent particles, more luminescent particles are aggregated; therefore, more beads and agglomerations are formed. Moreover, increasing percentage of the luminescent particles causes the porosity of the luminescent scaffold become low.

Moreover, the average diameter of electrospun nanofibers was determined using 20 different fibers and 100 different segments of the SEM captured images. For each fiber sample, measurements were carried out on 5 different pictures.

Figure 6A:
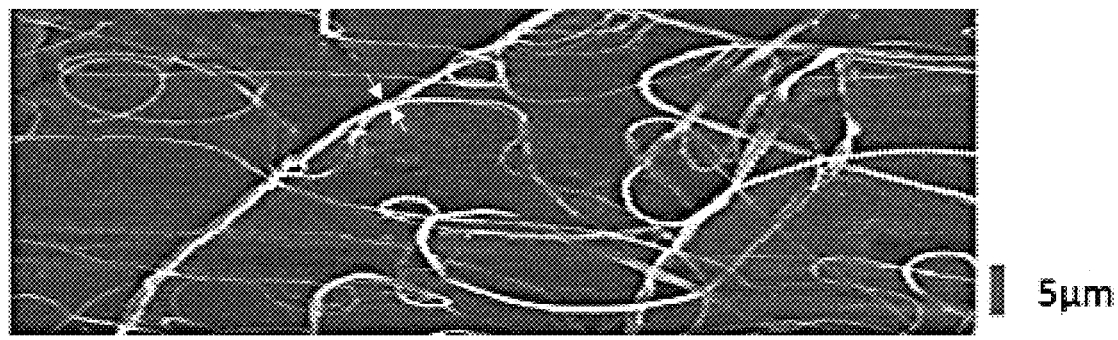
FIG. 6A illustrates a scanning electron microscopy (SEM) image of CS-PCL scaffold nanofibers, consistent with an exemplary embodiment of the present disclosure.

FIG. 6A illustrates a scanning electron microscopy (SEM) image of CS-PCL scaffold nanofibers, consistent with an exemplary embodiment of the present disclosure. Referring to FIG. 6A, the electrospun CS-PCL nanofibers are uniform and without any agglomeration in micro scale.

Figure 6B:
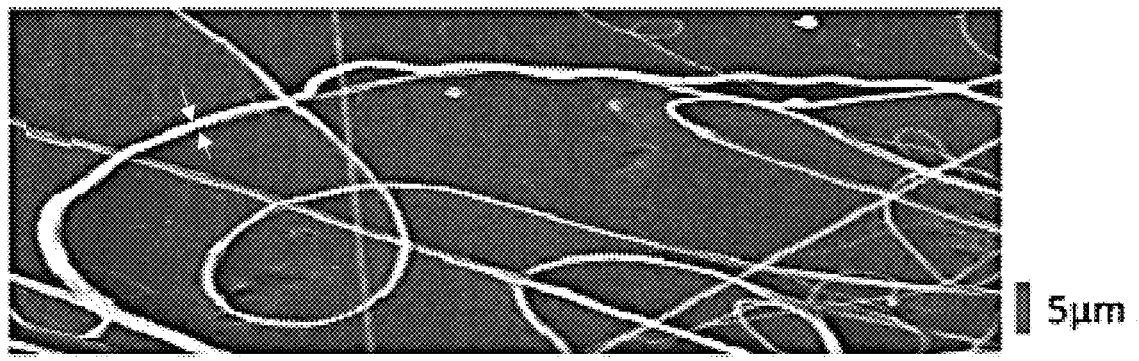
FIG. 6B illustrates a scanning electron microscopy (SEM) image of nanofibers of a $SrAl_2O_4:Eu^{2+}Dy^{3+}$/CS-PCL luminescent scaffold with 10% luminescent nanoparticles, consistent with an exemplary embodiment of the present disclosure.
Figure 6C:
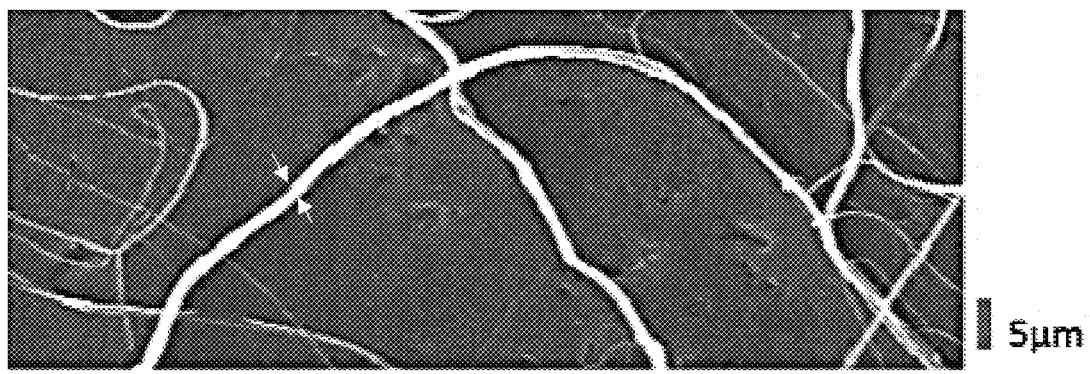
FIG. 6C illustrates a scanning electron microscopy (SEM) image of nanofibers of a $SrAl_2O_4:Eu^{2+}Dy^{3+}$/CS-PCL luminescent scaffold with 30% luminescent nanoparticles, consistent with an exemplary embodiment of the present disclosure.

FIG. 6B illustrates a scanning electron microscopy (SEM) image of nanofibers of the $SrAl_2O_4:Eu^{2+}Dy^{3+}$/CS-PCL luminescent scaffold with 10% luminescent particles. FIG. 6C illustrates a scanning electron microscopy (SEM) image of nanofibers of the $SrAl_2O_4$: $Eu^{2+}Dy^{3+}$/CS-PCL luminescent scaffold with 30% luminescent nanoparticles.

Figure 6D:
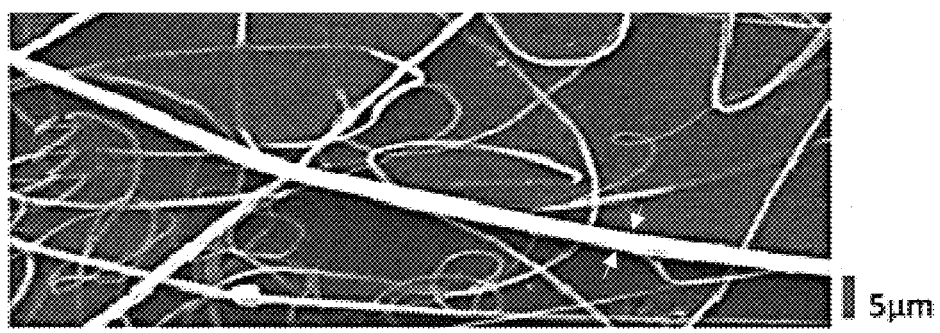
FIG. 6D illustrates a scanning electron microscopy (SEM) image of nanofibers of a $SrAl_2O_4:Eu^{2+}Dy^{3+}$/CS-PCL luminescent scaffold with 50% luminescent nanoparticles, consistent with an exemplary embodiment of the present disclosure.

FIG. 6D illustrates a scanning electron microscopy (SEM) image of nanofibers of the $SrAl_2O_4:Eu^{2+}Dy^{3+}$/CS-PCL luminescent scaffold with 50% luminescent nanoparticles. Referring to FIGS. 6B-6D, average diameter of the luminescent fibers is increased from 300-500 nm to 500-700 nm by increasing the percentage of the luminescent particles. Moreover, uniformity and consistency of nanofibers of the luminescent scaffold are decreased by increasing the percentage of the luminescent particles; on the other words, by increasing the dispersion of luminescent particles, fibers of the scaffold become thicker and plurality of beads and agglomerations are observable alongside of the fibers.

Figure 6E:
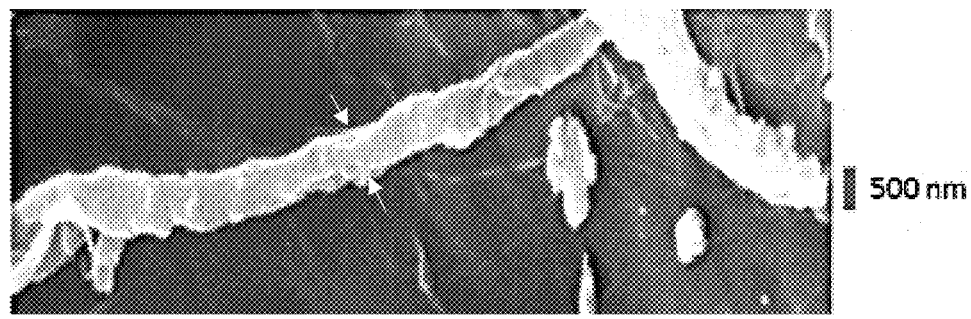
FIG. 6E illustrates a magnified scanning electron microscopy (SEM) image of nanofibers of a scaffold with 50% luminescent nanoparticles, consistent with an exemplary embodiment of the present disclosure.

FIG. 6E illustrates a magnified scanning electron microscopy (SEM) image of nanofibers of the scaffold with 50% luminescent nanoparticles. Referring to FIG. 6E, variable diameter sizes are observed throughout the luminescent fiber of the scaffold with 50% luminescent nanoparticles, due to the presence of the multiple agglomerations and beads of the luminescent particles in the fibers of the scaffold.

Example 3: Photoluminescence Properties of the Luminescent Scaffolds

In this example, photoluminescence properties of the luminescent nanoparticles and the prepared scaffolds are studied. Determination of photoluminescence properties of PEGylated $SrAl_2O_4:Eu^{2+}Dy^{3+}$ luminescent nanoparticles was done using Perking Elmer LS-55 fluorescence spectrophotometer with a 230 V pulsed Xenon source for excitation.

The samples were irradiated by UV light at a wavelength of 390 nm for 10 minutes prior to the emission measurements. After that, $SrAl_2O_4:Eu^{2+}Dy^{3+}$ luminescent nanoparticles were excited by a light beam with a prominent peak at a wavelength of 390 nm.

The emission spectra show a broad band peak at a wavelength of 512 nm which represents a transition from $4f^6 5d^1$ electron configuration to $4f^7$ electron configuration of excited $Eu^{2+}$ ions. While the typical emission peak of the luminescent particles is 520 nm, this shift towards shorter wavelengths, 512 nm, can be explained considering the sol-gel method in producing luminescent particles.

The sol-gel method produces nanoparticle form of the luminescent particles, which are much smaller in size in comparison with their common micro form; moreover, quantum size of the luminescent nanoparticles increases the kinetic energy of the electrons and a larger band gap; therefore, more energy is required to excite the luminescent nanoparticles and as a result the wavelength of the emitted light becomes shorter.

Figure 7:
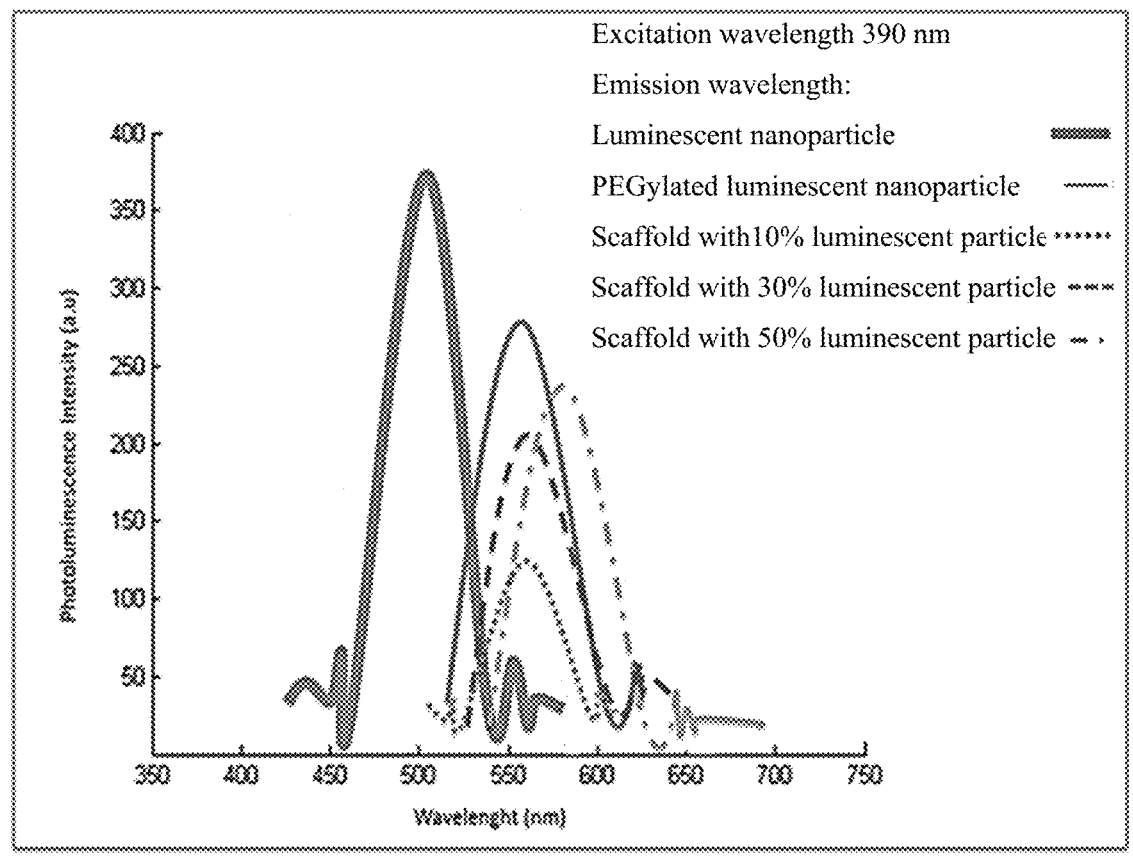
FIG. 7 illustrates excitation and emission spectra of $SrAl_2O_4:Eu^{2+}Dy^{3+}$ nanoparticles, PEGylated $SrAl_2O_4:Eu^{2+}Dy^{3+}$ luminescent nanoparticles and $SrAl_2O_4:Eu^{2+}Dy^{3+}$/CS-PCL luminescent scaffolds with 10%, 30% and 50% luminescent nanoparticles, consistent with an exemplary embodiment of the present disclosure.

FIG. 7 shows the excitation and emission spectra of coated and uncoated $SrAl_2O_4$: $Eu^{2+}Dy^{3+}$ luminescent nanoparticles and $SrAl_2O_4:Eu^{2+}Dy^{3+}$/CS-PCL scaffolds with 10%, 30% and 50% luminescent nanoparticles, consistent with an exemplary embodiment of the present disclosure.

Referring to FIG. 7, the luminescence characteristics of luminescent nanoparticles are presented before and after PEGylation. The wavelength shift, beyond 520 nm after PEGylation, as explained above, is due to the reverse relation of particle size and emitted light wavelength. Measurements show that sample particle size is increased from 20 nm to 120 nm after PEGylation which not only decreases the wavelength, but also attenuates the emission intensity significantly.

Referring back to FIG. 7, it can be concluded that the emission wavelengths of $SrAl_2O_4$: $Eu^{2+}Dy^{3+}$/CS-PCL scaffolds with 10%, 30% luminescent nanoparticles have no distinct variation from PEGylated $SrAl_2O_4:Eu^{2+}Dy^{3+}$ luminescent nanoparticles; but, PEGylated $SrAl_2O_4:Eu^{2+}Dy^{3+}$ luminescent nanoparticles have higher intensity of emission in comparison with $SrAl_2O_4:Eu^{2+}Dy^{3+}$/CS-PCL scaffolds with 10%, 30% luminescent nanoparticles.

Moreover, the intensity of emission for $SrAl_2O_4:Eu^{2+} Dy^{3+}$/CS-PCL scaffolds with 10%, luminescent nanoparticles is less than the $SrAl_2O_4:Eu^{2+}Dy^{3+}$/CS-PCL scaffolds with 30%, luminescent nanoparticles. This reduction in emission intensity can be related to the coating effect of the polymeric part of luminescent scaffold where it abates the excitation light reaching the luminescent particles.

As can be seen, the attenuation in emission intensity is redeemed by the adding the percentage of luminescent particles from 10% to 30% and 50%, for example in the $SrAl_2O_4$: $Eu^{2+}Dy^{3+}$/CS-PCL scaffolds with 50%, luminescent nanoparticles, there isn't any observable decrease in intensity of emission, but the wavelength has been shifted to longer ranges.

The luminescent particles when aggregated, produce particles which are more bulk; so as the percentage of the luminescent particles and resultantly, particle agglomeration increase, the wavelength shifts to longer values. As a result, the scaffold with 30% luminescent particles seems to be more biocompatible for both including shorter wavelength and middle intense emission.

Example 4: Mechanical Properties of the Luminescent Scaffold

In this example, mechanical properties of $SrAl_2O_4$:$Eu^{2+}$$Dy^{3+}$/CS-PCL luminescent scaffold are described. In order to determine the mechanical properties of $SrAl_2O_4$: $Eu^{2+}$$Dy^{3+}$/CS-PCL scaffold, tensile test was conducted by Instron 5882 Mechanical Testing System for all sample scaffolds. Measurements were done in a following condition: load cell was 50 kN, crosshead speed was constant until failure, and extension/compression rate was adjusted at 10 mm/min.

Figure 8:
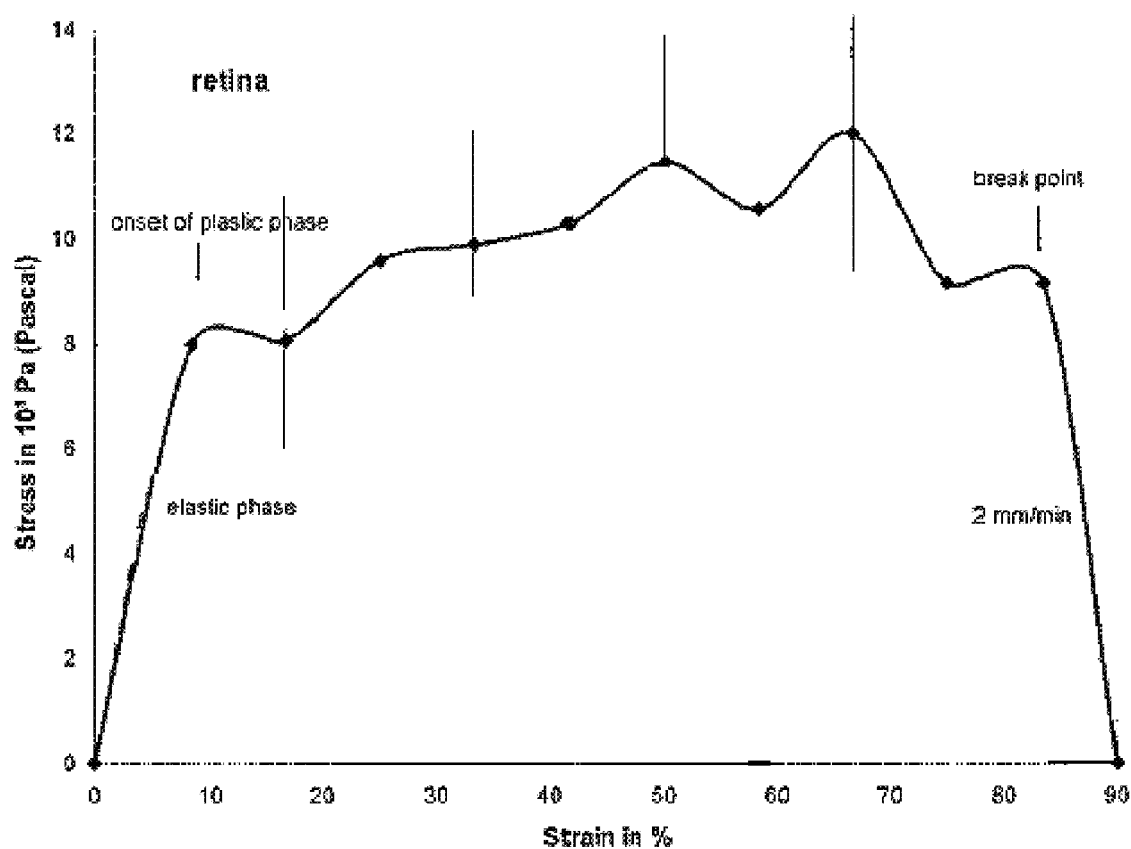
FIG. 8 illustrates a prior art standard stress-strain curves of retina, consistent with an exemplary embodiment of the present disclosure.
Figure 9:
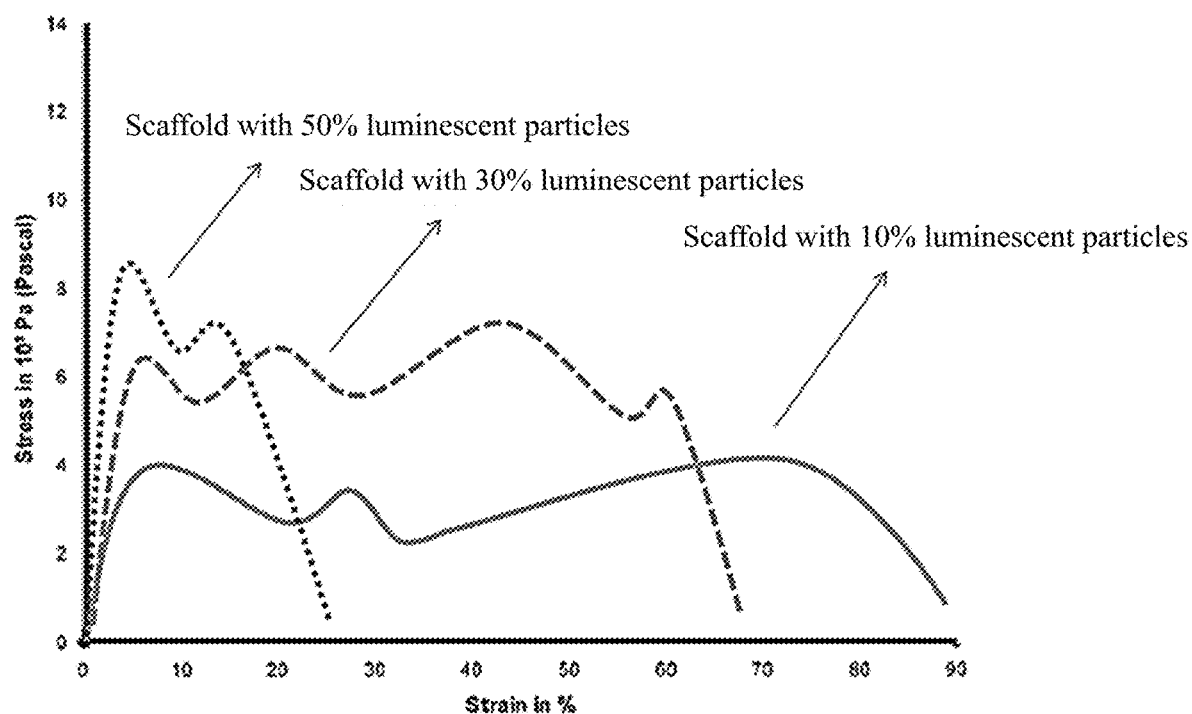
FIG. 9 illustrates stress-strain curves of $SrAl_2O_4:Eu^{2+}Dy^{3+}$/CS-PCL scaffolds with 10%, 30% and 50% luminescent nanoparticles, consistent with an exemplary embodiment of the present disclosure.

FIG. 8 illustrates a prior art graph of a standard stress-strain curve of retina with a biphasic mechanical behavior. FIG. 9 illustrates the stress-strain curves of $SrAl_2O_4$: $Eu^{2+}$$Dy^{3+}$/CS-PCL scaffolds with 10%, 30% and 50% luminescent nanoparticles with 2 mm/min strain rate. Referring to FIG. 8 and FIG. 9, the prepared scaffolds as test groups display the same mechanical behavior as the retina. The $SrAl_2O_4$:$Eu^{2+}Dy^{3+}$/CS-PCL scaffolds and the retina have a biphasic behavior with a short elastic phase and subsequently a proportionally wide plastic phase.

Referring again to FIG. 9, it is apparent that as the luminescent particle content in scaffolds increases, the flexibility of the luminescent scaffold reduces while the tensile strength increases. The luminescent scaffold with 50% luminescent nanoparticles can tolerate less deformation than other prepared scaffolds. Moreover, the luminescent scaffold with 10% of luminescent particles is quiet pliable and this luminescent scaffold has inadequate strength.

Referring back to FIG. 8 and FIG. 9, the luminescent scaffold with 30% of luminescent particles displays satisfactory mechanical strength and flexibility where its behavior is similar to the retinal tissue. Reduction in tissue elasticity during eye diseases such as macular degeneration leads to tissue tear and even permanent blindness; therefore, these scaffolds help to improve retina tissue endurance and retina tissue regeneration by preserving the retinal integrity.

Example 5: Biological Properties of the Luminescent Scaffold

In this example, biological properties of the luminescent nanoparticles and the prepared scaffolds were investigated. Monitoring the proliferation, differentiation, and morphology of mouse retina progenitor cells (mRPCs) was done on a cell line which was acquired from the Cell Therapy Center of Royan Institute. At first, the luminescent scaffolds, which were prepared in EXAMPLE 2, were sterilized under an ultraviolet lamp for 20 minutes at room temperature; then, they were rinsed with phosphate-buffered saline (PBS) for three times and immersed in the culture medium for 2 hours at a temperature of 37° C. prior to cell seeding.

Confluent low passage mRPCs GFP$^+$ cells were detached using Trypsin/EDTA solution with a concentration of 1.25% (weight/weight). Cultured mRPCs GFP$^+$ were further dissociated into single cell suspensions and seeded at a density of $3\times10^3$ cells per well onto all prepared $SrAl_2O_4$:$Eu^{2+}Dy^{3+}$/CS-PCL luminescent scaffolds with a total volume of 1 mL of culture medium. After that, the proliferation and attachment of cells on scaffolds were analyzed during a period of 7 days.

In order to analyze the cell behavior on the $SrAl_2O_4$:$Eu^{2+}$$Dy^{3+}$/CS-PCL luminescent scaffolds, seeded mRPCs on the $SrAl_2O_4$:$Eu^{2+}Dy^{3+}$/CS-PCL luminescent scaffolds were imaged using an Axio Observer Z1 inverted fluorescent microscope (Zeiss). Moreover, the scaffolds were imaged by a scanning electron microscope (SEM Philips XL30) which was operated at an acceleration voltage of 15 kV.

Cell attachment arises from protein adhesion molecules in a preliminary stage of proliferation. Particularly, fibronectin and vitronectin available in the complemented FBS, are known to promote cell adhesion; therefore, cell adhesion test was used to examine the cytological compatibility of the prepared $SrAl_2O_4$:$Eu^{2+}Dy^{3+}$/CS-PCL scaffolds.

Figure 10:
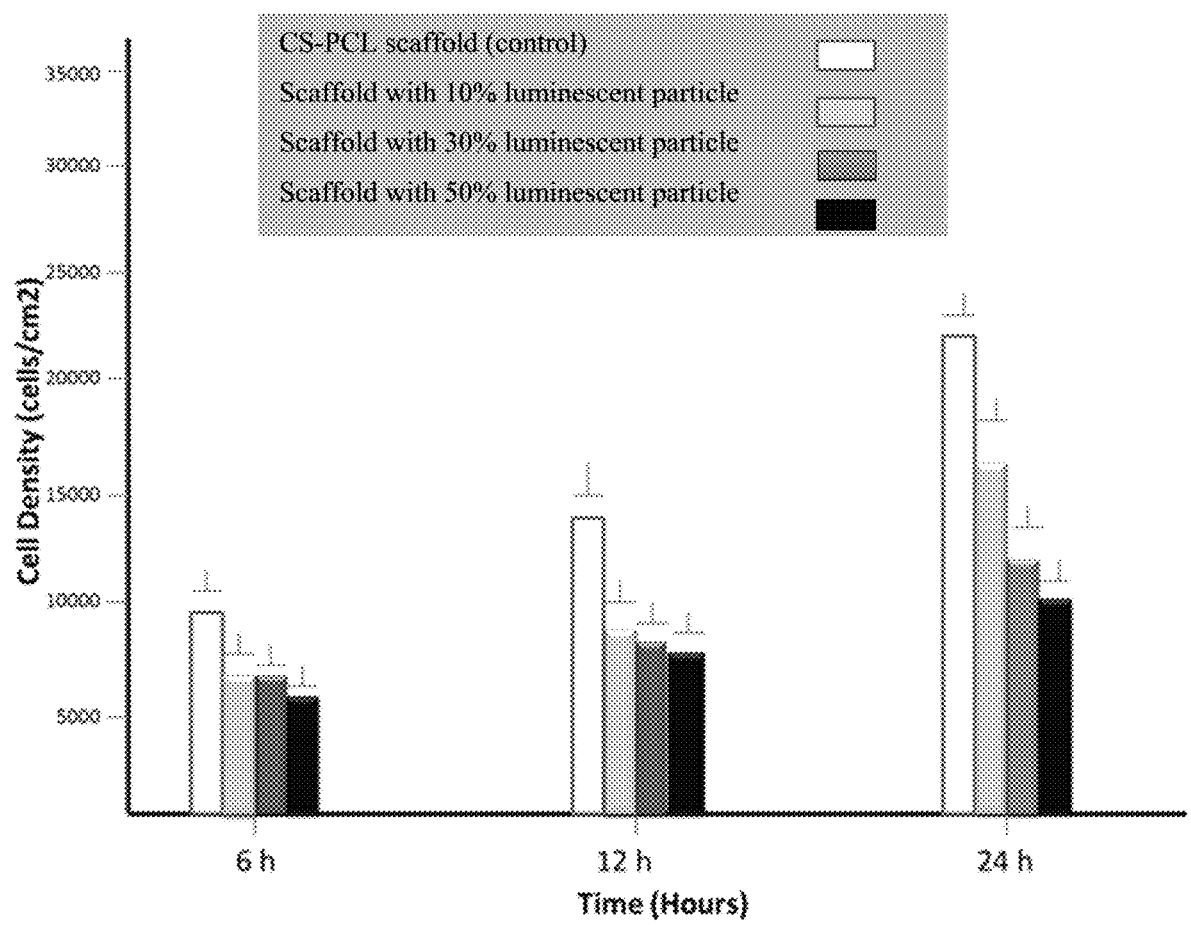
FIG. 10 illustrates cell density of mRPCs on a CS-PCL scaffold as a control group and $SrAl_2O_4:Eu^{2+}Dy^{3+}$/CS-PCL luminescent scaffolds after 6, 12 and 24 hours of cell culture, consistent with an exemplary embodiment of the present disclosure.

FIG. 10 illustrates density of mRPC cells attached to the surface of the CS-PCL scaffold as a control group and to the surfaces of $SrAl_2O_4$:$Eu^{2+}Dy^{3+}$/CS-PCL scaffolds as test groups for about 6, 12 and 24 hours after cell culture. Referring to FIG. 10, after 6 hours, there is not any significant difference between the sample scaffolds. As time passes, higher cell adhesion was observed in the scaffolds with no or less luminescent particles, for example CS-PCL scaffold and the scaffold with 10% luminescent particles.

This may relate to the fact that cells prefer hydrophilic surfaces for connection; therefore, by increasing the percentage of the luminescent particles in the scaffolds, the hydrophilicity of the surfaces of the scaffolds are decreased due to the gelatinous phase of the polymeric matrix of the scaffold.

Moreover cellular proliferation and differentiation of retinal cells for the control group and test groups were studied and the optimum emission for retinal cells growth and differentiation through luminescent scaffolds were determined.

Figure 11:
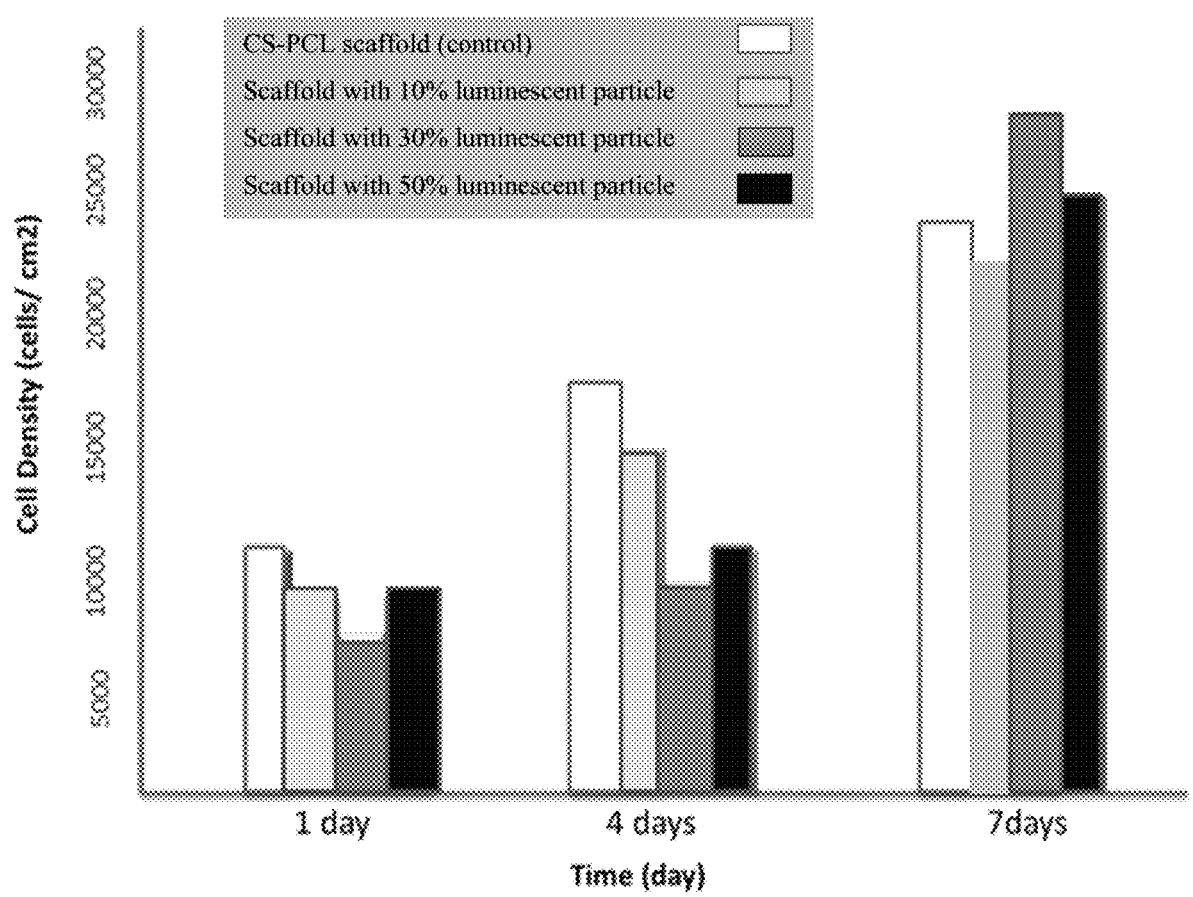
FIG. 11 illustrates cell density of mRPCs on a CS-PCL scaffold as a control group and $SrAl_2O_4:Eu^{2+}Dy^{3+}$/CS-PCL luminescent scaffolds as test groups after 1, 4 and 7 days of cell culture, consistent with an exemplary embodiment of the present disclosure.

FIG. 11 illustrates density of mRPCs attached to the surface of the CS-PCL scaffold as a control group and the $SrAl_2O_4$:$Eu^{2+}Dy^{3+}$/CS-PCL scaffolds as test groups for 1, 4 and 7 days after cell culture. Referring to FIG. 11, at first examination, cell proliferation was almost the same for all samples. Apparently, higher cell density shows higher proliferation of the cells. On the fourth day, while the luminescent scaffolds with 30% and 50% luminescent particles showed no tangible cell growth, the cell proliferation of the control group and the luminescent scaffold with 10% luminescent particles were almost doubled.

Referring back to FIG. 11, on the seventh day, the measurement displays a significant increase in cell population for scaffolds with a dispersion of 30% and 50% of the luminescent nanoparticles, while the control group and the luminescent scaffold with a dispersion of 10% of luminescent nanoparticles continue their linear growth with the same rate as the first half of the experiment. In general, the scaffold with the dispersion of 30% of the luminescent nanoparticles shows a promising result among all luminescent scaffolds with different luminescent particle dispersion.

Figure 12A:
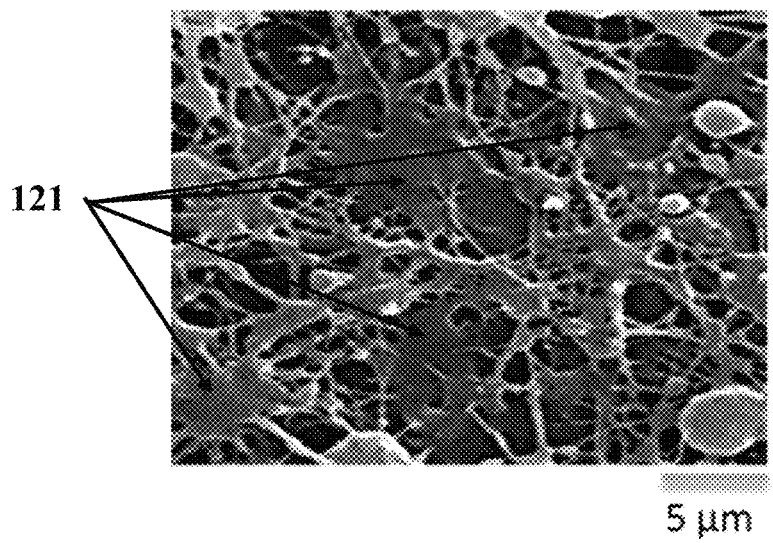
FIG. 12A illustrates a scanning electron microscopy (SEM) image of mRPCs cultured on a CS-PCL scaffold as a control group, consistent with an exemplary embodiment of the present disclosure.
Figure 12B:
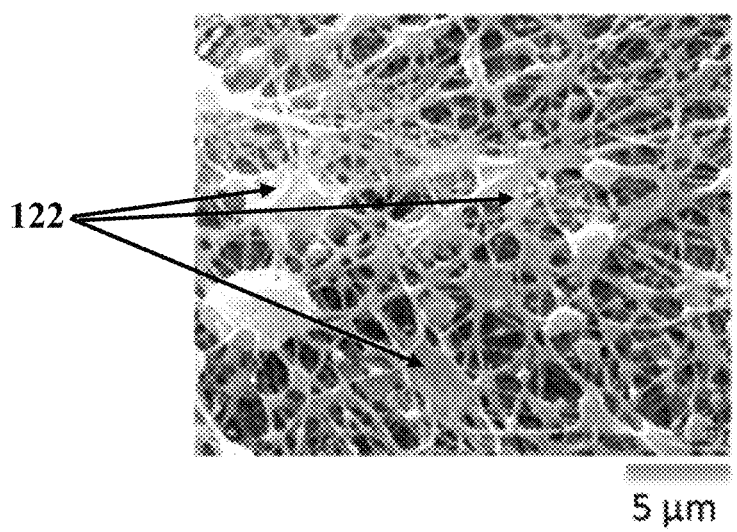
FIG. 12B illustrates a scanning electron microscopy (SEM) image of mRPCs cultured on a $SrAl_2O_4:Eu^{2+}Dy^{3+}$/CS-PCL luminescent scaffold with 10% luminescent nanoparticles, consistent with an exemplary embodiment of the present disclosure.

FIG. 12A illustrates the SEM micrograph of the mRPCs 121 cultured on the CS-PCL scaffold as a control group after four days of cell culture. FIG. 12B illustrates the SEM micrograph of the mRPCs 122 cultured on the $SrAl_2O_4$: $Eu^{2+}Dy^{3+}$/CS-PCL scaffold with 10% luminescent nanoparticles after four days of cell culture.

Figure 12C:
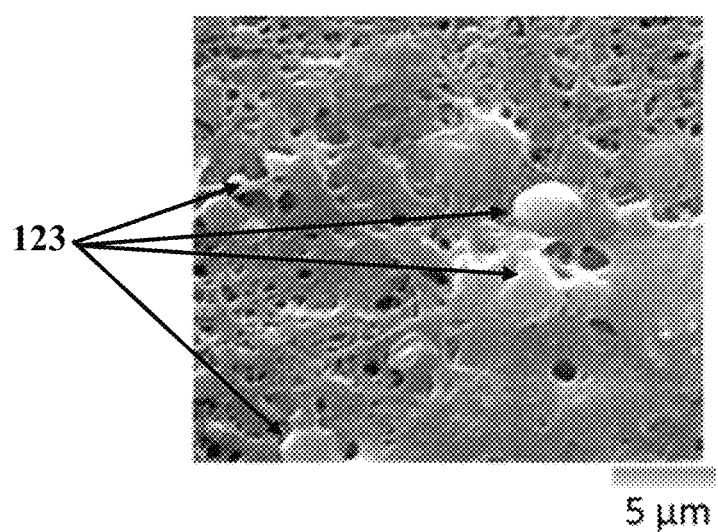
FIG. 12C illustrates a scanning electron microscopy (SEM) image of mRPCs cultured on a $SrAl_2O_4:Eu^{2+}Dy^{3+}$/CS-PCL luminescent scaffold with 30% luminescent nanoparticles, consistent with an exemplary embodiment of the present disclosure.
Figure 12D:
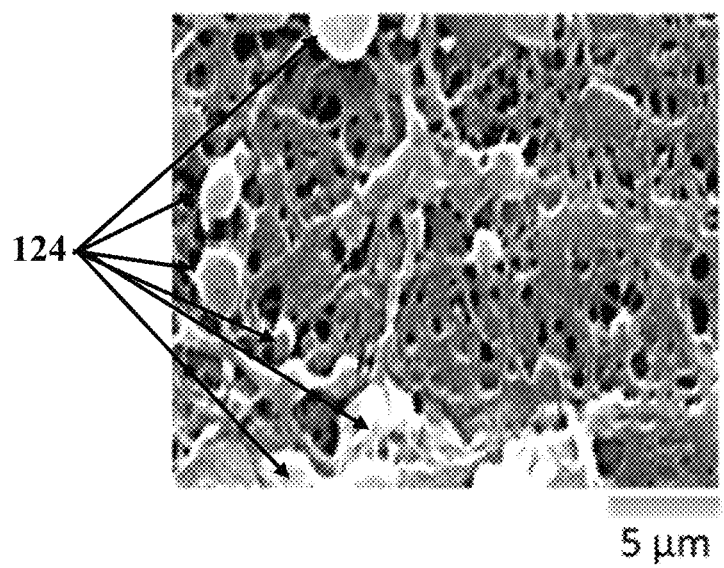
FIG. 12D illustrates scanning electron microscopy (SEM) images of mRPCs cultured on a $SrAl_2O_4:Eu^{2+}Dy^{3+}$/CS-PCL scaffold with 50% luminescent nanoparticles, consistent with an exemplary embodiment of the present disclosure.

FIG. 12C illustrates the SEM micrograph of the mRPCs 123 cultured on the $SrAl_2O_4$: $Eu^{2+}Dy^{3+}$/CS-PCL scaffold with 30% luminescent nanoparticles, after four days of cell culture. FIG. 12D illustrates the SEM micrograph of the mRPCs 124 cultured on the $SrAl_2O_4$: $Eu^{2+}Dy^{3+}$/CS-PCL scaffold with 50% luminescent nanoparticles after four days of cell culture.

Referring to FIGS. 12A-12D, it can be observed that most of the cells on scaffolds have a spherical and extended morphology that are bipolar or multipolar spreads. The tendency towards spherical morphology implies that emitting light from the luminescent scaffold may stimulate the cell signaling toward cell differentiation.

Figure 12E:
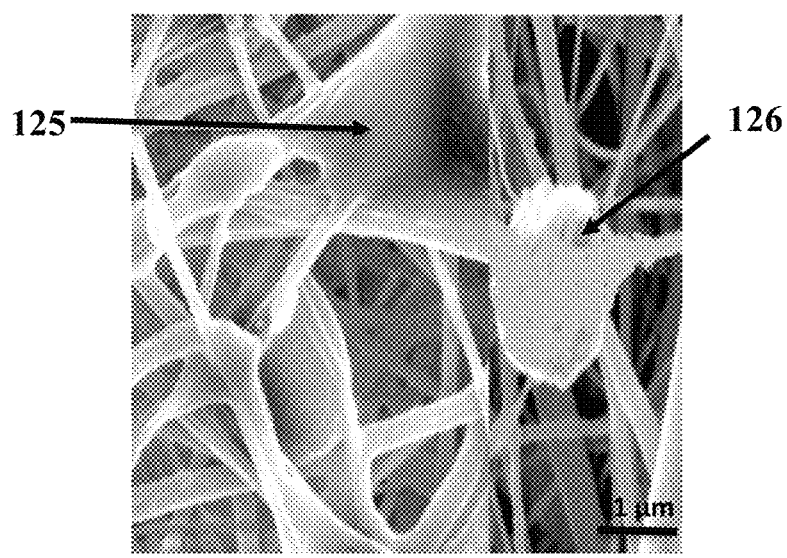
FIG. 12E illustrates a scanning electron microscopy (SEM) image of a cell which was grown on a $SrAl_2O_4:Eu^{2+}Dy^{3+}$/CS-PCL luminescent scaffold, consistent with an exemplary embodiment of the present disclosure.

FIG. 12E illustrates a scanning electron microscopy (SEM) image of a mRPC which was grown on the $SrAl_2O_4$: $Eu^{2+}Dy^{3+}$/CS-PCL luminescent scaffold. Referring to FIG. 12E, it can be concluded that mRPC cells 125 grow in sites of scaffolds which contains more luminescent nanoparticles 126 in the polymeric nanofibers; they have not grown directly on the luminescent nanoparticle, but cell proliferation around the points of nanoparticle accumulation in the scaffold is most evident.

In other words, cells 125 do not tend to stick and grow on luminescent nanoparticles 126, but growth and proliferation are observed in places close to those points where there is a emission of photons from the luminescent particles, and the growth of the cells is stabilized in these places. Various reasons such as the tendency of cells to attach on hydrophilic sites, and the effect of electromagnetic vibrations on the separation of cells from the surface can be attributed to this location and cell growth. Moreover, polarization of the sites with higher luminescent nanoparticle can affect the initial adhesion of the cells to these accumulation sites.

Moreover, effect of $SrAl_2O_4$:$Eu^{2+}Dy^{3+}$/CS-PCL luminescent scaffolds on mRPCs differentiation was also investigated under differentiation conditions through a quantitative polymerase chain reaction (qPCR). In the qPCR of the present experiment, expression of three important genes involving in retinal development were studied; these important genes were rhodopsin (a marker for rod photoreceptor cells), MAP2 (a marker for neuronal cells) and glial fibrillary acidic protein (GFAP, a glial marker).

The real-time PCR or qPCR was performed using a 7500 Real-Time PCR Detection System (Applied Biosystems, Carlsbad, Calif.) with 20 μL of total volume containing 10 μL of 2×SYBR PCR Premix EX Taq™ (Perfect Real Time; TaKaRa) and 10 μL of cDNA. Measured values for each culture condition are then evaluated for significance implementing the unpaired student t-test.

Figure 13A:
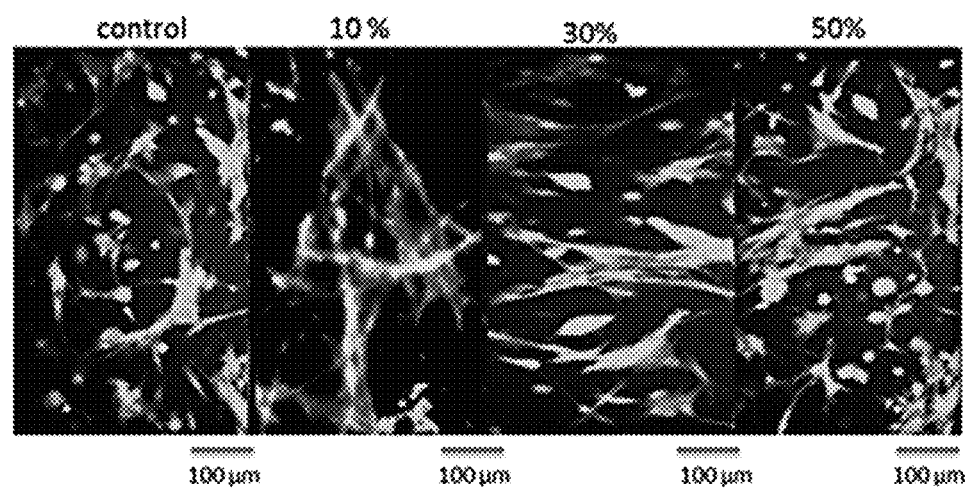
FIG. 13A illustrates florescence images of mRPCs cultured on different scaffolds containing 10%, 30% and 50% luminescent nanoparticles, consistent with an exemplary embodiment of the present disclosure.

FIG. 13A illustrates florescence images of mRPCs cultured on CS-PCL scaffold as a control group and on scaffolds containing 10%, 30% and 50% luminescent nanoparticles as test groups, consistent with an exemplary embodiment of the present disclosure. Referring FIG. 13A, the cells grown on the CS-PCL scaffold as a control group and on luminescent scaffolds with 10%, 30% and 50% luminescent nanoparticles as test groups display normal cell formations and healthy neurite outgrowth.

Figure 13B:
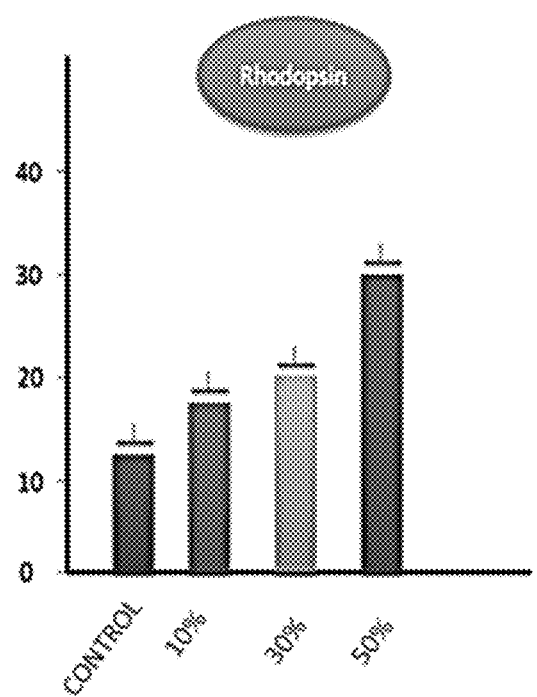
FIG. 13B illustrates expression levels of rhodopsin in the test groups and a control group, consistent with an exemplary embodiment of the present disclosure.

FIG. 13B illustrates the expression levels of rhodopsin, a marker of rod photoreceptor cells, in the cells grown on the CS-PCL scaffold as a control group and on the luminescent scaffolds with 10%, 30% and 50% luminescent nanoparticles as test groups, consistent with an exemplary embodiment of the present disclosure.

Referring to FIG. 13B, the expression of rhodopsin was increased by increasing the percentage of the luminescent particles in the scaffolds. Also, a prominent upregulation of rhodopsin with 3.1 fold is observed in the cells cultured on the scaffold with 50% luminescent nanoparticles in comparison with the control group.

Figure 13C:
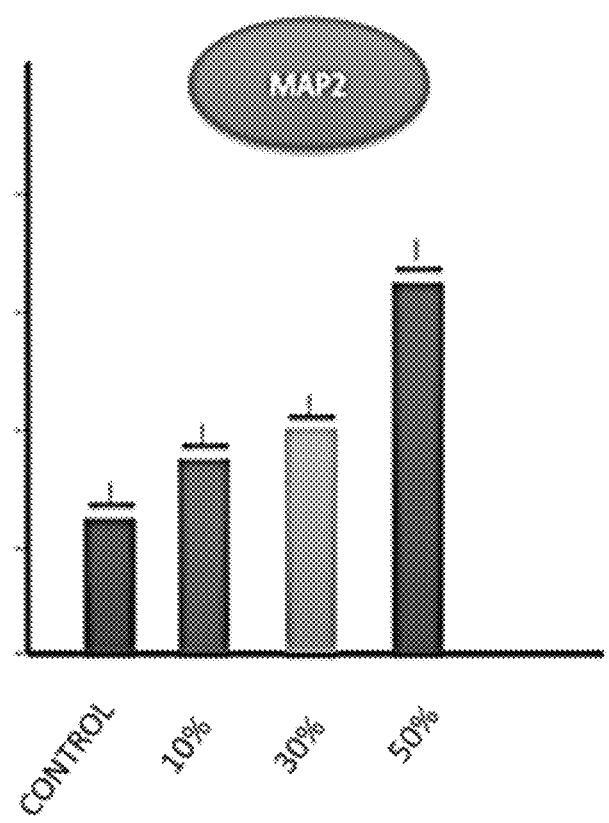
FIG. 13C illustrates expression levels of MAP2 in the test groups and a control group, consistent with an exemplary embodiment of the present disclosure.

FIG. 13C illustrates the expression levels of MAP2, a marker of neuronal cells, in the cells grown on the CS-PCL scaffold as a control group and on the luminescent scaffolds with 10%, 30% and 50% luminescent nanoparticles as test groups, consistent with an exemplary embodiment of the present disclosure. Referring to FIG. 13C, the expression of MAP2 was increased by increasing the percentage of the luminescent particles in the scaffolds. Also, a prominent upregulation of MAP2 with 2.9 fold is observed in the cells cultured on the scaffold with 50% luminescent nanoparticles in comparison with the control group.

Figure 13D:
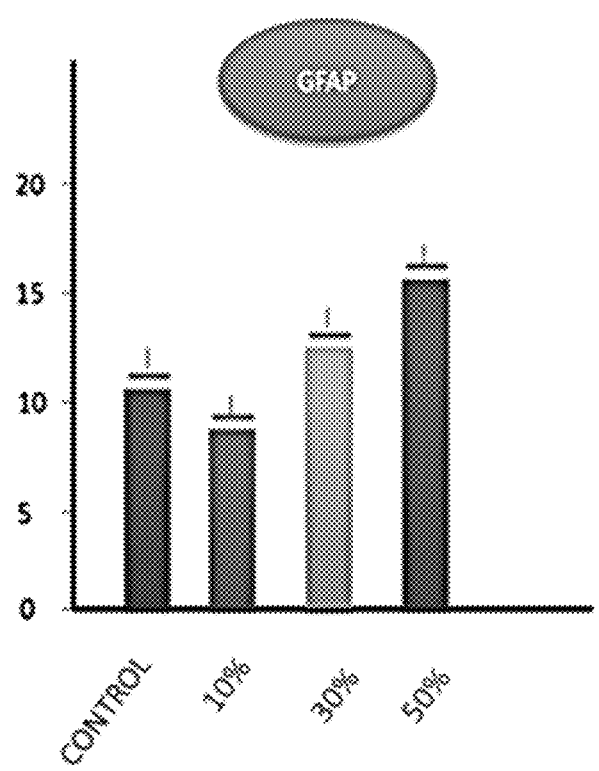
FIG. 13D illustrates expression levels of GFAP in the test groups and a control group, consistent with an exemplary embodiment of the present disclosure.

FIG. 13D illustrates the expression levels of GFAP, a glial marker, in the cells grown on the CS-PCL scaffold as a control group and on the luminescent scaffolds with 10%, 30% and 50% luminescent nanoparticles as test groups, consistent with an exemplary embodiment of the present disclosure. Referring to FIG. 13D, the expression level of GFAP in the cells of control group was lower than the expression level of GFAP in cells which were grown on scaffolds with 30% and 50% luminescent nanoparticles.

Cellular morphology and differentiation are affected by the characteristics of the surface on which the cells are growing. Also, the surface irregularity boosts differentiation. Referring back to FIGS. 13B-13D, increasing the percentage of luminescent particles in the scaffolds results in promoted cell differentiation; for example the scaffold with 50% luminescent particles significantly boosted mRPC proliferation and differentiation into retinal neural cells and particularly in photoreceptors cells.

The scaffold with 50% luminescent nanoparticles has an irregular surface due to the agglomeration of luminescent particles in compare to other scaffolds with less luminescent particles; therefore, this scaffold with 50% luminescent nanoparticles displays increased differentiation in comparison with other luminescent scaffolds.

Moreover, based on the results of the adhesion test and qPCR test, it can be concluded that using the scaffold with 50% luminescent nanoparticles in cell culture causes less cell attachment and it directs cells to their migratory state and to express more differentiation markers in comparison with the scaffolds with 10% and 30% luminescent nanoparticles.

These findings imply that mRPCs which were grown on the $SrAl_2O_4$:$Eu^{2+}Dy^{3+}$/CS-PCL scaffolds in differentiation conditions had been tend to differentiate toward retinal neuronal lineages, most notably, toward photoreceptor cells. Without being bound by any theory, the inventors believe that light emission from the luminescent scaffolds, which in turn leads to intracellular chemical reactions, and sensitive nature of neurogenesis to optical signals are effective incentives in retinal cell differentiation and retina regeneration.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for regenerating retinal tissue, comprising:
preparing a luminescent scaffold comprising:
synthesizing a plurality of luminescent particles;
dispersing the luminescent particles in a polymeric matrix to form a luminescent composite, the luminescent composite comprising the luminescent particles with a concentration between 5 mg/ml and 15 mg/ml; and
electrospinning the luminescent composite to form the luminescent scaffold;
implanting the luminescent scaffold in a portion of retina, the portion of the retina comprising subretinal area;
emitting a green light from the luminescent nanoparticles in a luminescence phenomenon; and
absorbing the emitted light by retinal cells for regenerating retinal tissue by stimulating the retinal cells.

2. The method of claim 1, wherein dispersing the luminescent particles in the polymeric matrix comprises dispersing the luminescent particles in the polymeric matrix using a homogenizer, a stirrer, an agitator, a sonicator, an ultrasound device, or combinations thereof.

3. The method of claim 1, wherein electrospinning the luminescent composite comprises feeding the luminescent composite through an electrospinning column with a feeding rate of 1 mL/hour.

4. The method of claim 3, wherein the luminescent particles are biocompatible particles and are PEGylated by polyethylene glycol (PEG).

5. The method of claim 1, wherein electrospinning the luminescent composite comprises pumping the luminescent composite into an electrospinning column, wherein the electrospinning column comprise a needle with a gauge of 17.

6. The method of claim 1, wherein electrospinning the luminescent composite comprises applying an electric field with a strength of 15 kV/20 cm between an electrospinning column and a collecting plate.

7. The method of claim 1, wherein the luminescent scaffold further comprises polyethylene glycol (PEG).

8. The method of claim 7, wherein the polyethylene glycol (PEG) is present in the luminescent scaffold with a concentration between 5 mg/ml and 15 mg/ml.

9. The method of claim 7, wherein the polyethylene glycol (PEG) is present in the luminescent scaffold with a concentration of 10 mg/ml.

10. The method of claim 1, wherein the luminescent particles are luminescent nanoparticles.

11. The method of claim 1, wherein the luminescent particles are ceramic particles.

12. The method of claim 1, wherein the luminescent particles includes one of $SrAl_2O_4: Eu^{2+}Dy^3$ particles, $NaYF_4:Yb^{3+}Er^{3+}$ particles, and combinations thereof.

13. The method of claim 1, wherein synthesizing the plurality of luminescent particles comprises synthesizing the plurality of luminescent particles using one of sol gel method, co-precipitation method, and combinations thereof.

14. The method of claim 1, wherein the polymeric matrix includes a copolymer of polycaprolactone (PCL) and chitosan (CS).

15. A method for regenerating retinal tissue, comprising:
preparing a luminescent scaffold comprising:
synthesizing a plurality of luminescent particles;
forming a luminescent composite by dispersing the luminescent particles and polyethylene glycol (PEG) in a polymeric, the luminescent composite comprising the PEG with a concentration between 5 mg/ml and 15 mg/ml; and
forming a luminescent scaffold by electrospinning the luminescent composite;
implanting the luminescent scaffold in a subretinal area;
emitting a green light from the luminescent nanoparticles in a luminescence phenomenon; and
absorbing the emitted light by retinal cells for regenerating retinal tissue by stimulating the retinal cells.

16. The method of claim 15, wherein the luminescent particles includes one of $SrAl_2O_4:Eu^{2+}Dy^3$ particles, $NaYF_4:Yb^{3+}Er^{3+}$ particles, and combinations thereof.

17. A method for regenerating retinal tissue, comprising:
preparing a luminescent scaffold comprising:
synthesizing a plurality of luminescent particles;
forming a luminescent composite by dispersing the luminescent particles in a polymeric matrix; and
forming a luminescent scaffold by electrospinning the luminescent composite, the electrospinning the luminescent composite comprises feeding the luminescent composite through an electrospinning column with a feeding rate of 1 mL/hour;
implanting the luminescent scaffold in a subretinal area;
emitting a green light from the luminescent nanoparticles in a luminescence phenomenon; and
absorbing the emitted light by retinal cells for regenerating retinal tissue by stimulating the retinal cells.

18. The method of claim 17, wherein the luminescent composite comprises the luminescent particles with a concentration between 5 mg/ml and 15 mg/ml.

19. The method of claim 17, wherein the luminescent particles includes one of $SrAl_2O_4:Eu^{2+}Dy^3$ particles, $NaYF_4:Yb^{3+}Er^{3+}$ particles, and combinations thereof.

* * * * *